US008617548B2

(12) United States Patent
Casey

(10) Patent No.: US 8,617,548 B2
(45) Date of Patent: Dec. 31, 2013

(54) METHODS OF PREVENTING OR TREATING ANTHRAX USING ANTI-ANTHRAX ANTIBODIES

(75) Inventor: Leslie S. Casey, New York, NY (US)

(73) Assignee: Elusys Therapeutics, Inc., Pine Brook, NJ (US)

( * ) Notice: Subject to any disclaimer, the term of this patent is extended or adjusted under 35 U.S.C. 154(b) by 0 days.

(21) Appl. No.: 13/076,082

(22) Filed: Mar. 30, 2011

(65) Prior Publication Data

US 2012/0156196 A1 Jun. 21, 2012

Related U.S. Application Data

(62) Division of application No. 11/904,882, filed on Sep. 28, 2007, now Pat. No. 8,093,360.

(60) Provisional application No. 60/848,480, filed on Sep. 28, 2006.

(51) Int. Cl.
*A61K 39/40* (2006.01)

(52) U.S. Cl.
USPC .................. 424/133.1; 424/141.1; 424/150.1; 424/164.1

(58) Field of Classification Search
None
See application file for complete search history.

(56) References Cited

U.S. PATENT DOCUMENTS

| | | | |
|---|---|---|---|
| 5,470,570 A | 11/1995 | Taylor et al. | |
| 5,487,890 A | 1/1996 | Taylor et al. | |
| 5,585,089 A | 12/1996 | Queen et al. | |
| 5,914,112 A | 6/1999 | Bednar et al. | |
| 7,601,351 B1 * | 10/2009 | Rosen et al. | 424/139.1 |
| 2003/0235818 A1 | 12/2003 | Katritch et al. | |
| 2004/0180046 A1 | 9/2004 | Himawan | |
| 2005/0221284 A1 | 10/2005 | Taylor et al. | |

FOREIGN PATENT DOCUMENTS

| | | |
|---|---|---|
| WO | 92/05801 A1 | 4/1992 |
| WO | 98/52976 A1 | 11/1998 |
| WO | 00/34317 A2 | 6/2000 |
| WO | 01/80883 A1 | 11/2001 |
| WO | 03/063768 A2 | 8/2003 |
| WO | 2004/110362 A2 | 12/2004 |
| WO | 2005/023177 A2 | 3/2005 |
| WO | 2006/096039 A1 | 9/2006 |

OTHER PUBLICATIONS

Bendig (Methods: A Companion to Methods in Enzymology 1995; 8:83-93).*
Karginov et al (FEMS Immunology and Medical Microbiology, 40:71-74, 2004).*
Mohamed et al (Infection and Immunity, 73(2):795-802, Feb. 2005).*
Maynard et al (Nature Biotechnology, 20:597-601, Jun. 2002).*
Brookmeyer, Ron et al., "Modelling the incubation period of anthrax," Statistics in Medicine, vol. 24:531-542 (2005).
Cieslak, Theodore J. et al., "Clinical and Epidemiologic Principles of Anthrax," Emerging Infectious Diseases, vol. 5 (4):552-555 (1999).
Comer, Jason E. et al., "Direct Inhibition of T-Lymphocyte Activation by Anthrax Toxins in Vivo," Infection and Immunity, vol. 73(12):8275-8281 (2005).
Cummins, Larry M. et al., "Preparation and Characterization of an Intravenous Solution of IgG from Human Immunodeficiency Virus-Seropositive Donors," Blood, vol. 77(5):1111-1117 (1991).
Dixon, Terry C. et al., "Anthrax," New England Journal of Medicine, vol. 341(11):815-826 (1999).
During, Russell L. et al., "Anthrax Lethal Toxin Paralyzes Neutrophil Actin-Based Motility," The Journal of Infectious Diseases, vol. 192:837-845 (2005).
Erwin, James L. et al., "Macrophage-Derived Cell Lines Do Not Express Proinflammatory Cytokines after Exposure to *Bacillus anthracis* Lethal Toxin," Infection and Immunity, vol. 69(2):1175-1177 (2001).
Fang, Hui et al., "Anthrax Lethal Toxin Has Direct and Potent Inhibitory Effects on B Cell Proliferation and Immunoglobulin Production," The Journal of Immunology, vol. 176:6155-6161 (2006).
Holty, Jon-Erik C. et al., "Systematic Review: A Century of Inhalational Anthrax Cases from 1900-2005," Ann. Intern. Med., vol. 144:270-280 (2006).
Jernigan, John A. et al., "Bioterrorism-Related Inhalational Anthrax: The First 10 Cases Reported in the United States," Emerging Infectious Diseases, vol. 7(6):933-944 (2001).
Jones, S.M. et al., "Complete Protection against *Staphylococcus aureus* Bacteremia Using a Novel Dual Antibody Therapeutic Approach," 44th Interscience Conference on Antimicrobial Agents and Chemotherapy, Abstract No. F-724, 2 Pages (2004).
Lim, Nam-Kyu et al., "An Anthrax Lethal Factor-Neutralizing Monoclonal Antibody Protects Rats before and after Challenge with Anthrax Toxin," Infection and Immunity, vol. 73(10):6547-6551 (2005).
Little, Stephen F. et al., "Production and Characterization of Monoclonal Antibodies to the Protective Antigen Component of *Bacillus anthracis* Toxin," Infection and Immunity, vol. 56(7):1807-1813 (1988).
Mascola, John R. et al., "Potent and Synergistic Neutralization of Human Immunodeficiency Virus (HIV) Type 1 Primary Isolates by Hyperimmune Anti-HIV Immunoglobulin Combined with Monoclonal Antibodies 2F5 and 2G12," Journal of Virology, vol. 71(10):7198-7206 (1997).
O'Brien, John et al., "Effects of Anthrax Toxin Components on Human Neutrophils," Infection and Immunity, vol. 47 (1):306-310 (1985).
Peterson, Johnny W. et al., "Human Monoclonal Anti-Protective Antigen Antibody Completely Protects Rabbits and Is Synergistic with Ciprofloxacin in Protecting Mice and Guinea Pigs against Inhalation Anthrax," Infection and Immunity, vol. 74(2):1016-1024 (2006).

(Continued)

*Primary Examiner* — Patricia A Duffy
(74) *Attorney, Agent, or Firm* — Nelson Mullins Riley & Scarborough LLP; Debra J. Milasincic, Esq.

(57) ABSTRACT

The present invention provides an antibody which binds to *B. anthracis* with toxin, formulations for administration of such antibodies intramuscularly, and methods of administering such antibodies prophylactically or therapeutically.

21 Claims, 5 Drawing Sheets

(56) References Cited

OTHER PUBLICATIONS

PR Newswire Association, LLC, "Elusys Presents Positive Data on Anthrax Therapeutic at ICAAC," 2 pages (2006).

Rivera, Johanna et al., "A Monoclonal Antibody to *Bacillus anthracis* Protective Antigen Defines a Neutralizing Epitope in Domain 1," Infection and Immunity, vol. 74(7):4149-4156 (2006).

Taylor, Ronald P. et al., "In Vivo Binding and Clearance of Circulating Antigen by Bispecific Heteropolymer-mediated Binding to Primate Erythrocyte Complement Receptor," The Journal of Immunology, vol. 148(8):2462-2468 (1992).

Taylor, Ronald P. et al., "Use of heteropolymeric monoclonal antibodies to attach antigens to the C3b receptor of human erythrocytes: A potential therapeutic treatment," Proc. Natl. Acad. Sci. USA, vol. 88:3305-3309 (1991).

Zhao, Ping et al., "Neutralizing monoclonal antibody against Anthrax lethal factor inhibits intoxication in a mouse model," Human Antibodies, vol. 12:129-135 (2003).

International Search Report for Application No. PCT/US2007/020934, 7 pages, dated Apr. 10, 2008.

International Preliminary Report on Patentability and Written Opinion for Application No. PCT/US2007/020934, 8 pages, dated Mar. 31, 2009.

* cited by examiner

A. Males

B. Females

Figure 4

| | Group | IV, 5 mg/kg | IM, 5 mg/kg | IM, 10 mg/kg |
|---|---|---|---|---|
| Males | Cmax, μg/mL | N/A | 40.3 ± 4.7 | 94.9 ± 13.8 |
| | Tmax[a], d | N/A | 2.5 (1-6) | 0.8 (0.3-1.3) |
| | AUC(0-inf), μg·d/mL | 752.5 ± 106.0 | 614.4 ± 63.5 | 1285.0 ± 64.2 |
| | Clearance, L/d/kg | 0.007 ± 0.001 | N/A | N/A |
| | Vss, L/kg | 0.090 ± 0.051 | N/A | N/A |
| | T$_{1/2}$[b], d | 7.9 ± 3.3 | 6.8 ± 2.9 | 8.4 ± 2.2 |
| | F, % | N/A | 81.65 | 85.38 |
| Females | Cmax, μg/mL | N/A | 40.3 ± 7.8 | 75.6 ± 18.5 |
| | Tmax[a], d | N/A | 1.3 (0.08-1.3) | 1.3 (1.3-4.0) |
| | AUC(0-inf), μg·d/mL | 717.8 ± 153.7 | 481.8 ± 86.5 | 1399.5 ± 99.6 |
| | Clearance, L/d/kg | 0.007 ± 0.001 | N/A | N/A |
| | Vss, L/kg | 0.092 ± 0.010 | N/A | N/A |
| | T$_{1/2}$[b], d | 9.7 ± 1.6 | 6.0 ± 2.0 | 12.0 ± 1.9 |
| | F, % | N/A | 67.12 | 97.48 |

[a] Median and range
[b] Harmonic mean and pseudo SD based on jackknife variance
N/A - Not Applicable

Figure 5

Anti-PA Heavy Chain (SEQ ID No:1)

Anti-PA Light Chain (SEQ ID No:2)

SEQUENCE LISTING

<160> NUMBER OF SEQ ID NOS: 16

<210> SEQ ID NO 1
<211> LENGTH: 449
<212> TYPE: PRT
<213> ORGANISM: Artificial Sequence
<220> FEATURE:
<223> OTHER INFORMATION: Chemically synthesized anti-PA antibody (heavy chain)

<400> SEQUENCE: 1

Gln Val Gln Leu Gln Gln Ser Gly Pro Glu Leu Lys Lys Pro Gly Ala
1               5                   10                  15

Ser Val Lys Val Ser Cys Lys Asp Ser Gly Tyr Ala Phe Ser Ser Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Asp Thr Asn Tyr Asn Gly Lys Phe
    50                  55                  60

Gln Gly Arg Val Thr Ile Thr Ala Asp Lys Ser Ser Ser Thr Ala Tyr
65                  70                  75                  80

Met Glu Leu Ser Ser Leu Arg Ser Glu Asp Thr Ala Val Tyr Phe Cys
                85                  90                  95

Ala Arg Ser Gly Leu Leu Arg Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Cys Gln Pro Arg Glu Pro Gln Val Tyr Thr
            340                 345                 350

```
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys

<210> SEQ ID NO 2
<211> LENGTH: 213
<212> TYPE: PRT
<213> ORGANISM: Artificial Sequence
<220> FEATURE:
<223> OTHER INFORMATION: Chemically synthesized anti-PA antibody (light
      chain)

<400> SEQUENCE: 2

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Arg Asn Tyr
            20                  25                  30
Leu Asn Trp Tyr Gln Gln Lys Pro Gly Lys Ala Val Lys Leu Leu Ile
        35                  40                  45
Tyr Tyr Thr Ser Arg Leu Leu Pro Gly Val Pro Ser Arg Phe Ser Gly
    50                  55                  60
Ser Gly Ser Gly Thr Asp Tyr Ser Leu Thr Ile Ser Ser Gln Glu Gln
65                  70                  75                  80
Glu Asp Ile Gly Thr Tyr Phe Cys Gln Gln Gly Asn Thr Leu Pro Trp
                85                  90                  95
Thr Phe Gly Gln Gly Thr Lys Val Glu Ile Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210

<210> SEQ ID NO 3
<211> LENGTH: 20
<212> TYPE: PRT
<213> ORGANISM: Artificial Sequence
<220> FEATURE:
```

```
<223> OTHER INFORMATION: Chemically synthesized peptide:  linker
      sequence

<400> SEQUENCE: 3

Gly Gly Gly Gly Ser Gly Gly Gly Ser Gly Gly Gly Gly Ser Gly
1               5                   10                  15

Gly Gly Gly Ser
            20

<210> SEQ ID NO 4
<211> LENGTH: 11
<212> TYPE: PRT
<213> ORGANISM: Artificial Sequence
<220> FEATURE:
<223> OTHER INFORMATION: Chemically synthesized peptide:  CDR L1 of
      murine 14B7

<400> SEQUENCE: 4

Arg Ala Ser Gln Asp Ile Arg Asn Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Chemically synthesized peptide:  CDR L2 of
      murine 14B7

<400> SEQUENCE: 5

Tyr Thr Ser Arg Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Chemically synthesized peptide:  CDR L3 of
      murine 14B7

<400> SEQUENCE: 6

Gln Gln Gly Asn Thr Leu Pro Trp Thr
1               5

<210> SEQ ID NO 7
<211> LENGTH: 9
<212> TYPE: PRT
<213> ORGANISM: Artificial Sequence
<220> FEATURE:
<223> OTHER INFORMATION: Chemically synthesized peptide:  CDR H1 of
      murine 14B7

<400> SEQUENCE: 7

Tyr Ala Phe Ser Ser Ser Trp Met Asn
1               5

<210> SEQ ID NO 8
<211> LENGTH: 17
<212> TYPE: PRT
<213> ORGANISM: Artificial Sequence
<220> FEATURE:
<223> OTHER INFORMATION: Chemically synthesized peptide:  CDR H2 of
      murine 14B7

<400> SEQUENCE: 8

Arg Ile Tyr Pro Gly Asp Gly Asp Thr Asn Tyr Asn Gly Lys Phe Lys
1               5                   10                  15
```

-continued

Gly

<210> SEQ ID NO 9
<211> LENGTH: 10
<212> TYPE: PRT
<213> ORGANISM: Artificial Sequence
<220> FEATURE:
<223> OTHER INFORMATION: Chemically synthesized peptide: CDR H3 of
      murine 14B7

<400> SEQUENCE: 9

Ser Gly Leu Leu Arg Tyr Ala Met Asp Tyr
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Chemically synthesized peptide: CDRL2

<400> SEQUENCE: 10

Tyr Thr Ser Arg Leu Leu Pro
1               5

<210> SEQ ID NO 11
<211> LENGTH: 17
<212> TYPE: PRT
<213> ORGANISM: Artificial Sequence
<220> FEATURE:
<223> OTHER INFORMATION: Chemically synthesized peptide: CDRH2

<400> SEQUENCE: 11

Arg Ile Tyr Pro Gly Asp Gly Asp Thr Asn Tyr Asn Gly Lys Phe Gln
1               5                   10                  15

Gly

<210> SEQ ID NO 12
<211> LENGTH: 11
<212> TYPE: PRT
<213> ORGANISM: Artificial Sequence
<220> FEATURE:
<223> OTHER INFORMATION: Chemically synthesized peptide: FR4 region of
      the light chain

<400> SEQUENCE: 12

Phe Gly Gly Gly Thr Lys Leu Glu Ile Arg Arg
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Chemically synthesized peptide: FR4 region of
      the light chain

<400> SEQUENCE: 13

Phe Gly Gly Gly Thr Lys Leu Glu Ile Lys Arg
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Chemically synthesized peptide: CDRL2

```
<400> SEQUENCE: 14

Tyr Thr Ser Arg Leu Gln Pro
1               5

<210> SEQ ID NO 15
<211> LENGTH: 7
<212> TYPE: PRT
<213> ORGANISM: Artificial Sequence
<220> FEATURE:
<223> OTHER INFORMATION: Chemically synthesized peptide:   CDRL2

<400> SEQUENCE: 15

Tyr Thr Ser Arg Leu Ala Ser
1               5

<210> SEQ ID NO 16
<211> LENGTH: 10
<212> TYPE: PRT
<213> ORGANISM: Artificial Sequence
<220> FEATURE:
<223> OTHER INFORMATION: Chemically synthesized peptide:   CDRH3

<400> SEQUENCE: 16

Ser Gly Ala Leu Arg Tyr Ala Met Asp Tyr
1               5                   10
```

METHODS OF PREVENTING OR TREATING ANTHRAX USING ANTI-ANTHRAX ANTIBODIES

RELATED APPLICATIONS

This application is a Divisional application of U.S. application Ser. No. 11/904,882 filed Sep. 28, 2007 which claims priority to U.S. provisional application Ser. No. 60/848,480 filed Sep. 28, 2006, the contents of which are entirely incorporated by reference.

GOVERNMENT FUNDING

Work described herein was supported, at least in part, under grant Challenge Grant 1-UC1-AI062546-01, awarded by NIAID and Naval Research Laboratory Contract N00173-04-C-2028. The U.S. government, therefore, may have certain rights in this invention.

BACKGROUND OF THE INVENTION

Anthrax is primarily a disease of sheep, cattle, horses, goats and swine caused by *Bacillus anthracis*, a gram-positive spore-forming aerobic rod that produces exotoxins. The organism is transmitted to humans by inoculation of broken skin or mucous membranes causing cutaneous or gastrointestinal infections, or by inhalation, causing pulmonary infection. Anthrax is a rare occupational disease of farmers, veterinarians and wool workers. *B. anthracis* is designated as category A biothreat agent because of the ease of weaponization of spores and its persistence in the environment. The bioterrorism threat from inhaled *B. anthracis* spores has increased the need for effective treatments and preventions of this deadly disease.

Inhalation anthrax is the most deadly form of the disease. The incubation period ranges from 1-43 days, with a mean incubation period of 16 days (Cieslak et al., 1999). The standard course of antibiotic treatment post-exposure is 60 days, but the length of treatment for full protection is currently unknown. The mean duration of non-specific prodromal symptoms is 4.1 days, and the mean duration of the fulminant phase is 1.1 days, after which the death rate approaches 100% in the absence of treatment (Holty et al. 2006). The events leading to death from anthrax in humans are not well understood (Jernigan et al. 2001), but the terminal stages of the disease involve bacteremia with vascular damage and injury to multiple organs. Anthrax pathogenesis has been reviewed (Dixon et al. 1999).

*B. anthracis* produces two exotoxins, Edema Toxin (EdTx) and Lethal Toxin (LeTx). During the initial phases of the disease, the toxins cause destruction of the lymphatic tissue, helping the bacteria gain access to the blood stream (Dixon et al., 1999). They also impair the function of leukocytes that are crucial for phagocytosis and mounting an immune response (O'Brien et al. 1985; Comer et al. 2005; During et al. 2005; Erwin et al. 2001; Fang et al. 2006). EdTx is composed of Edema Factor (EF) and Protective Antigen (PA), and LeTx is composed of Lethal Factor (LF) and PA. As single entities, none of these proteins are known to have any lethal effects. PA is the essential component for EF and LF entry into target cells. PA binds to specific receptors on the host cell surface and after activation by a furin-like protease, forms a heptamer complex and binding sites for either EF or LF are created. The complex (PA+LF or PA+EF) is then taken into the cell via clathrin mediated endocytosis. Upon acidification in the endosomes, the PA heptamer changes conformation, inserts in the membrane forming a channel and allows the two factors to enter the cytosol.

Victims of inhalational anthrax do not experience significant symptoms until a late stage in the disease when they are close to sepsis and toxemia. Antibiotic treatment is largely ineffective at the symptomatic stage in preventing death (Holty et al. 2006), in part because antibiotics do not target the anthrax toxins. To be maximally effective, antibiotic therapy must be initiated within hours of exposure to aerosolized *B. anthracis* spores, prior to the onset of symptoms (Holty et al. 2006). However, in the event of mass exposure to anthrax spores, as could occur in a bioterrorist attack, treatment would most likely not begin until 3 to 6 days post-exposure, on average, owing to the length of time required to identify potential victims and distribute stockpiled medication (Brookmeyer 2005). At that point, upwards of 25% of anthrax cases following exposure to a lethal dose of anthrax spores would fail to be prevented by antibiotics alone (Brookmeyer et al. 2005). Anthrax vaccines, which over the course of several weeks stimulate the immune system to mount a protective response against PA, are effective in pre-exposure prophylaxis, and can afford some protection from breakthrough infection arising from germination of residual spores after withdrawal of antibiotic therapy. Anthrax vaccines are ineffective when used alone in the post-exposure setting.

An area of unmet need for anthrax is fast-acting medical countermeasures to infection with antimicrobial-resistant strains. The development of such agents would be of great benefit.

SUMMARY OF THE INVENTION

The present invention provides an antibody which binds to the toxin produced by *B. anthracis* with high affinity, formulations appropriate for administration of such antibodies, e.g., intramuscularly, and methods of administering such antibodies prophylactically or therapeutically.

In one aspect, the invention provides a method of preventing the development of inhalation anthrax in a human subject that has been exposed to *B. anthracis* spores, the method comprising administering intramuscularly a composition comprising an antibody which neutralizes *B. anthracis* toxin to the subject and further comprising administering at least one antibiotic to the subject to thereby preventing the development of inhalation anthrax in a human subject that has been exposed to *B. anthracis* spores.

In another aspect, the invention provides a method of preventing the development of inhalation anthrax in a human subject prior to exposure to *B. anthracis* spores, the method comprising administering intramuscularly a composition comprising an antibody which neutralizes *B. anthracis* toxin to the subject and further comprising administering at least one antibiotic to the subject to thereby preventing the development of inhalation anthrax in a human subject that prior to exposure to *B. anthracis* spores.

In yet another aspect, the invention provides a method of treating inhalation anthrax in a human subject that has been exposed to *B. anthracis* spores, the method comprising administering intramuscularly a composition comprising an antibody which neutralizes *B. anthracis* toxin to the subject and further comprising administering at least one antibiotic to the subject to thereby treat inhalation anthrax in a human subject that has been exposed to *B. anthracis* spores.

In one embodiment of the invention, the antibody has a $K_d$ of 2 nM to 15 nM. In another embodiment, the antibody is deimmunized. In another embodiment, the antibody comprises a human Fc region. In yet another embodiment, the human Fc region is of the IgG1 isotype.

In one embodiment, the antibody comprises at least one CDR derived from the murine 14B7 antibody. In another embodiment, the antibody comprises the CDRs of the murine 14B7 antibody. In another embodiment, the antibody comprises the six CDRs shown in FIG. 5. In yet another embodiment, the antibody comprises the light chain variable region and the heavy chain variable region amino acid sequence shown in FIG. 5. In one embodiment, the antibody comprises the amino acid sequence shown in FIG. 5.

In one embodiment, the antibody is given at a dose of 20-50 mg intramuscularly. In another embodiment, the antibody is given at a dose of 30-50 mg intramuscularly. In another embodiment, the antibody is given at a dose of at least about 38 mg intramuscularly.

In one embodiment, the antibody is administered 3 hours after exposure to exposure to B. anthracis spores. In another embodiment, the antibody is administered 6 hours after exposure to exposure to B. anthracis spores. In another embodiment, the antibody is administered 9 hours after exposure to exposure to B. anthracis spores. In yet another embodiment, the antibody is administered 12 hours after exposure to exposure to B. anthracis spores. In yet another embodiment, the antibody is administered 15 hours after exposure to exposure to B. anthracis spores. In another embodiment, the antibody is administered 18 hours after exposure to exposure to B. anthracis spores. In one embodiment, the antibody is administered 24 hours after exposure to exposure to B. anthracis spores. In another embodiment, the antibody is administered 36 hours after exposure to exposure to B. anthracis spores.

In one embodiment of the invention, the antibiotic is a fluoroquinolone antibiotic. In another embodiment, the fluoroquinolone antibiotic is levofloxacin. In another embodiment, the fluoroquinolone antibiotic is ciprofloxacin.

In another aspect, the invention provides a composition comprising an antibody which binds to protective antigen (PA) of B. anthracis with high affinity and is formulated for intramuscular administration.

In one embodiment, the antibody is high affinity. In another embodiment, the antibody is deimmunized. In another embodiment, the antibody comprises a human Fc region. In yet another embodiment, the human Fc region is of the IgG1 isotype. In another embodiment, the antibody comprises at least one CDR derived from the murine 14B7 antibody. In yet another embodiment, the antibody comprises the CDRs of the murine 14B7 antibody. In another embodiment, the antibody comprises the six CDRs shown in FIG. 5. In one embodiment, the antibody comprises the light chain variable region and the heavy chain variable region amino acid sequence shown in FIG. 5. In another embodiment, the antibody comprises the amino acid sequence shown in FIG. 5.

In one embodiment, the antibody is formulated at a concentration of at least about 10 mg/ml. In another embodiment, the antibody is formulated at a concentration of 12.5 mg/ml. In yet another embodiment, the antibody is given in a dose of at least about 30 mg. In another embodiment, the antibody is given at a dose of at least about 38 mg.

In another aspect, the invention provides an antibody or antigen binding portion thereof comprising the six CDRs shown in FIG. 5.

In yet another aspect, the invention provides an antibody or antigen binding portion thereof comprising the light chain variable region and the heavy chain variable region amino acid sequence shown in FIG. 5.

In another aspect, the invention provides an antibody comprising the amino acid sequence shown in FIG. 5.

BRIEF DESCRIPTION OF THE FIGURES

FIG. 4 shows the pharmacokinetics of anti-PA antibody in cynomolgus monkeys. The terminal T1/2 of the anti-PA by both routes was 7.9 (males) to 9.7 (females) days. The bioavailability of IM anti-PA averaged 83% as compared to IV administration. No significant difference in pharmacokinetics was observed based on gender, except for AUC in the 5 mg/kg IM dose group. AUC (area under the curve) is a measure of the bioavailability of the antibody and represents the body's total exposure over time to the anti-PA antibody. AUC (0-inf), which indicates the average AUC from time zero to infinity, was linear by dose. The bioavailability of the claimed anti-PA antibody by the IM route in monkeys was similar to that of the IV route.

FIG. 5 shows the amino acid sequence of the heavy chain (SEQ ID NO:1) and the light chain (SEQ ID NO:2) of an anti-PA antibody.

DETAILED DESCRIPTION OF THE INVENTION

Figure 1:
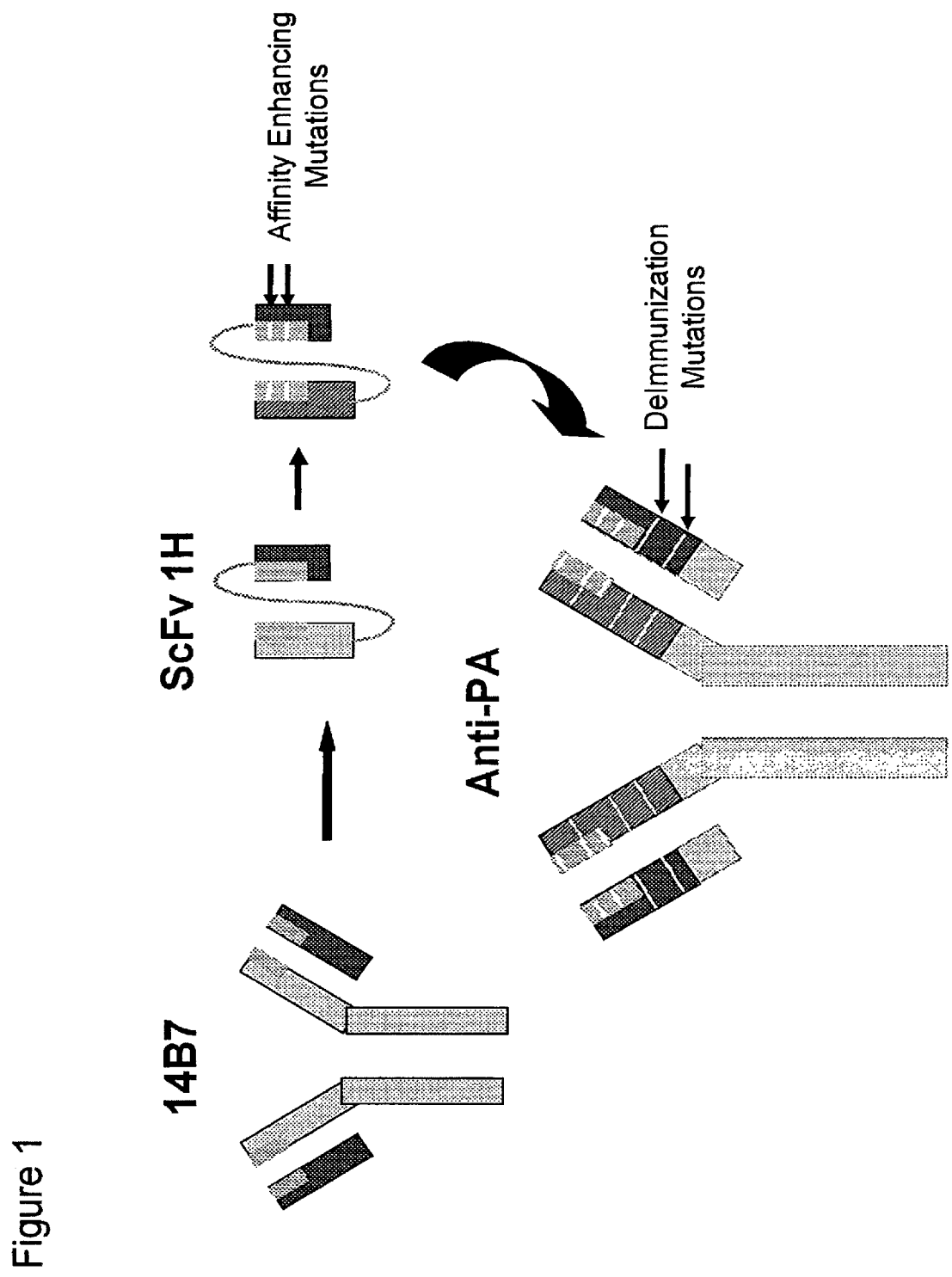
FIG. 1 is an overview of the method for generating a high-affinity anti-PA antibody. The progenitor of the anti-PA antibody was murine anti-PA MAb 14B7 (Little et al., 1988). The mouse variable (V) regions of MAb 14B7 were affinity-enhanced (Maynard et al. 2002). The affinity-enhanced V regions were re-engineered into a chimeric MAb with human gamma 1 (IgH) and Kappa (IgL) constant regions, followed by further modifications to the variable regions to minimize immunogenic potential.
Figure 2:
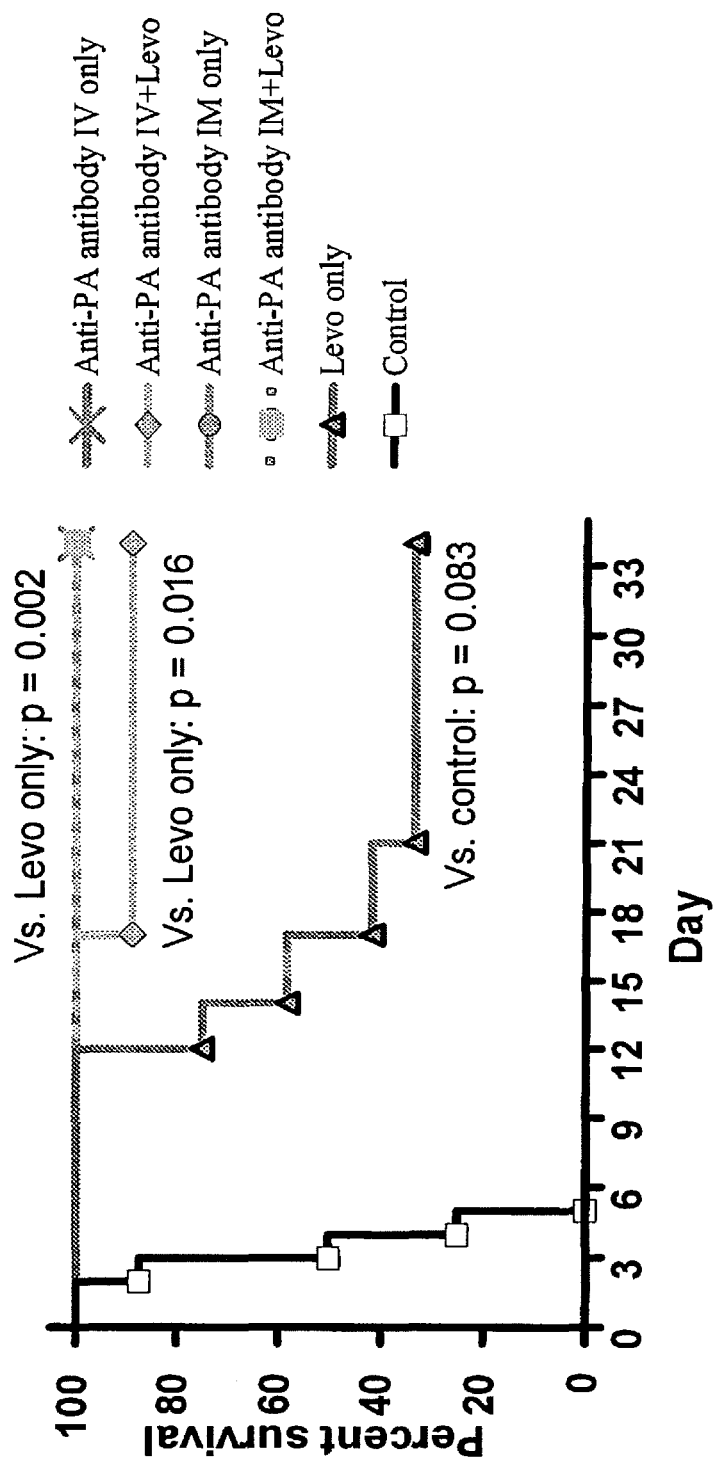
FIG. 2 shows a comparison of survival of rabbits after anthrax spore challenge and co-administration of the anti-protective antigen antibodies and a fluoroquinolone antibiotic. None of the rabbits in the control group survived past day 5. Treatment of rabbits with levofloxacin only led to increased survival. However, treatment of rabbits with anti-PA antibody (either intravenously or intramuscularly) in combination with levofloxacin led to a significant increase in survival of the rabbits.
Figure 3:
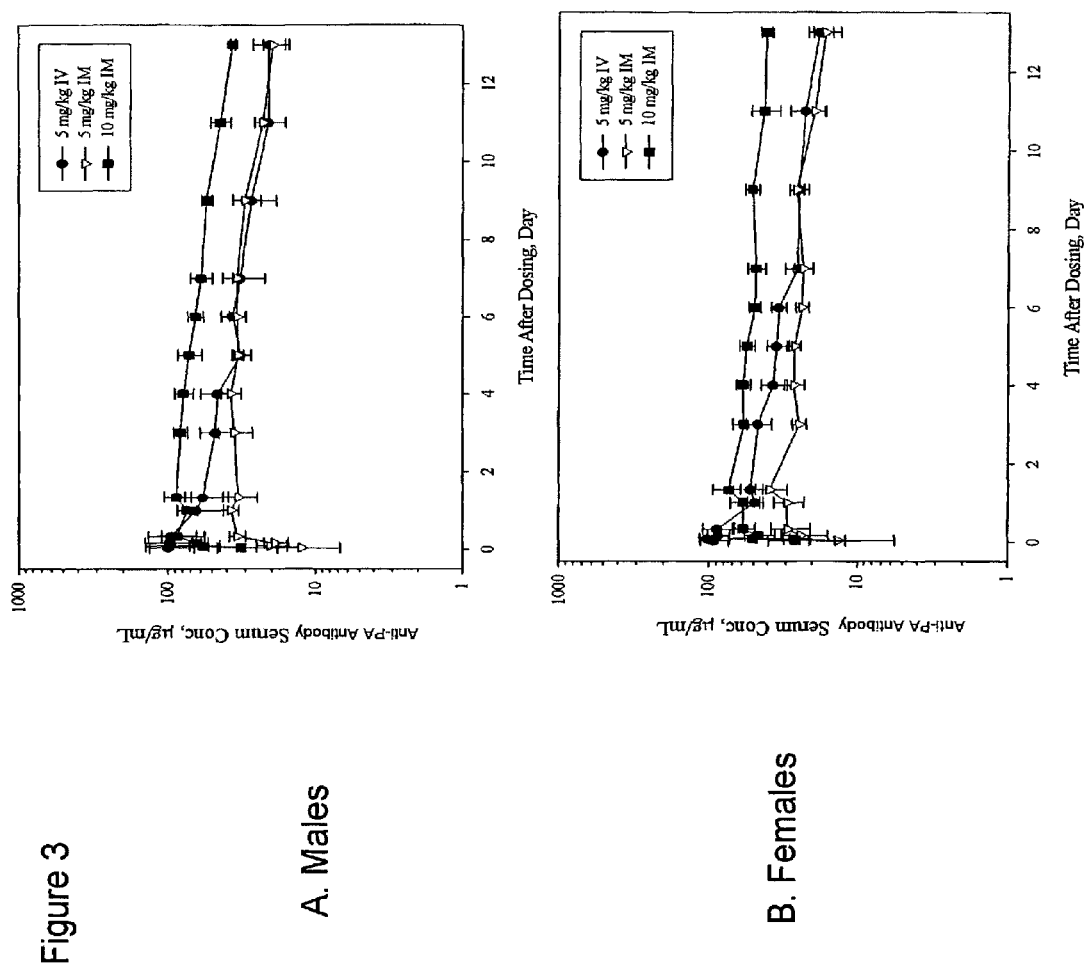
FIG. 3 shows the results of a primate study to determine the pharmacokinetics of the anti-protective antigen antibody delivered by the intravenous or intramuscular routes.

*Bacillus anthracis* is a spore-forming, gram-positive bacterium that causes anthrax. Upon entry through the skin, ingestion, or inhalation, *B. anthracis* spores germinate into vegetative bacteria. A tripartite exotoxin secreted from the bacteria represents a key virulence factor in anthrax. The anthrax PA component of the exotoxin mediates the host cell entry of the two other components, the lethal factor (LF), a zinc metalloprotease that cleaves several mitogen-activated protein kinase kinases, and the edema factor, a calmodulin-dependent adenylate cyclase. Structures of all three proteins have been determined. In addition, the mechanisms by which the PA-LF complex (lethal toxin [LeTx]) enters the cell have been identified along with the chronology with which these events occur. The protective antigen binds to two cell surface receptors, ATR and CMG2, and suggests that the CMG2 gene is expressed in most human tissues and, recently, the ATR/TEM8 gene was reported to be highly expressed in epithelial cells.

For persons infected with anthrax, treatment success is limited by several factors, such as the increased incidence of antibiotic resistance and treatment delays that lessen the chance of survival. It is known that early treatment of anthrax with antibiotics is essential to reduce mortality-delays in treatment profoundly decrease survival rates. Early treatment, however, is difficult because initial symptoms of the infection, e.g., when the bacterial spores are inhaled, heretofore known as inhalation anthrax, may resemble those of the common cold. In addition, symptoms of anthrax infection, depending on how the bacterium is contracted, may take seven to sixty days to appear.

The invention described herein provides a method of treating subjects who have been exposed to anthrax or anthrax spores or are risk of exposure, by neutralization of anthrax toxin, e.g., by binding to PA or LF. The subject anti-anthrax antibodies are of high affinity, are neutralizing, and have a half life sufficient to reduce the symptoms of inhalation anthrax either alone, or in combination with additional agents. The subject antibodies are effective both prophylactically and therapeutically.

Accordingly, the present invention provides antibodies which bind to the toxin produced by *B. anthracis*, formulations appropriate for administration of such antibodies, and methods of administering such antibodies to subjects, preferably human subjects, prophylactically or therapeutically, by various routes of administration e.g., intramuscularly.

Before further description of the invention, certain terms are defined.

I. Definitions

The antibodies may be naturally occurring or modified antibodies which bind to the toxin produced by *Bacillus anthracis*.

As used herein the term "derived from" a designated protein refers to the origin of the polypeptide. In one embodiment, the polypeptide or amino acid sequence which is derived from a particular starting polypeptide is a CDR sequence or sequence related thereto. In one embodiment, the amino acid sequence which is derived from a particular starting polypeptide is not contiguous. For example, in one embodiment, one, two, three, four, five, or six CDRs are derived from a starting antibody. In one embodiment, the polypeptide or amino acid sequence which is derived from a particular starting polypeptide or amino acid sequence has an amino acid sequence that is essentially identical to that of the starting sequence, or a portion thereof wherein the portion consists of at least of at least 3-5 amino acids, 5-10 amino acids, at least 10-20 amino acids, at least 20-30 amino acids, or at least 30-50 amino acids, or which is otherwise identifiable to one of ordinary skill in the art as having its origin in the starting sequence. In one embodiment, the one or more CDR sequences derived from the starting antibody are altered to produce variant CDR sequences, wherein the variant CDR sequences maintain antigen binding activity.

It will also be understood by one of ordinary skill in the art that the binding molecules of the invention may be modified such that they vary in amino acid sequence from the molecule from which they were derived, e.g., the 14B7 molecule. For example, nucleotide or amino acid substitutions leading to conservative substitutions or changes at "non-essential" amino acid residues may be made (e.g., in non-essential CDR and/or framework residues). The binding molecules of the invention maintain the ability to bind to anthrax toxin. In one embodiment, such mutations increase the binding affinity for the antigen. In another embodiment, the mutations decrease the immunogenicity of the anti-anthrax antibody.

An isolated nucleic acid molecule encoding a non-natural variant of a polypeptide can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide may be replaced with another amino acid residue from the same side chain family. In another embodiment, a string of amino acids can be replaced with a structurally similar string that differs in order and/or composition of side chain family members.

Alternatively, in another embodiment, mutations may be introduced randomly along all or part of the immunoglobulin coding sequence.

In one embodiment, the binding molecules comprise one binding site. In another embodiment, the binding molecules comprise at least two antigen binding sites. In one embodiment, the binding molecules comprise two antigen binding sites. In one embodiment, the binding molecules comprise three antigen binding sites. In another embodiment, the binding molecules comprise four antigen binding sites.

In one embodiment, the binding molecules of the invention are monomers. In another embodiment, the binding molecules of the invention are multimers. For example, in one embodiment, the binding molecules of the invention are dimers. In one embodiment, the dimers of the invention are homodimers, comprising two identical monomeric subunits. In another embodiment, the dimers of the invention are heterodimers, comprising two non-identical monomeric subunits. The subunits of the dimer may comprise one or more polypeptide chains. For example, in one embodiment, the dimers comprise at least two polypeptide chains. In one embodiment, the dimers comprise two polypeptide chains. In another embodiment, the dimers comprise four polypeptide chains (e.g., as in the case of antibody molecules).

Preferred binding molecules of the invention comprise framework and constant region amino acid sequences derived from a human amino acid sequence. However, binding polypeptides may comprise framework and/or constant region sequences derived from another mammalian species. For example, a primate framework region (e.g., non-human primate), heavy chain portion, and/or hinge portion may be included in the subject binding molecules. In one embodiment, one or more murine amino acids may be present in the framework region of a binding polypeptide, e.g., a human or non-human primate framework amino acid sequence may comprise one or more amino acid back mutations in which the corresponding murine amino acid residue is present. Preferred binding molecules of the invention do not provoke a delterious immune response, e.g., are less immunogenic than murine antibodies.

The term "antibody" as used herein refers to immunoglobulin molecules. The term "antibody" includes complete antibody molecules as well as antigen binding portions thereof. Immunoglobulin molecules are encoded by genes which include the kappa, lambda, alpha, gamma, delta, epsilon and mu constant regions, as well as a myriad of immunoglobulin variable regions. Light chains are classified as either kappa or lambda. Light chains comprise a variable light ($V_L$) and a constant light ($C_L$) domain. Heavy chains are classified as gamma, mu, alpha, delta, or epsilon, which in turn define the immunoglobulin classes IgG, IgM, IgA, IgD and IgE, respectively. Heavy chains comprise variable heavy ($V_H$), constant heavy 1 ($C_H1$), hinge, constant heavy 2 ($C_H2$), and constant heavy 3 ($C_H3$) domains. The IgG heavy chains are further sub-classified based on their sequence variation, and the sub-classes are designated IgG1, IgG2, IgG3 and IgG4. The term "antibody" includes, e.g., naturally occurring antibody or immunoglobulin molecules or modified (e.g., genetically engineered) antibody molecules that resemble naturally occurring antibody molecules. The term "antibody" as used herein also includes modified forms of antibody molecules, e.g., scfv molecules, minibodies, and the like. An antibody of the invention can belong to any one of these classes and/or isotypes.

The term "antigen-binding portion" or "antigen binding fragment" of an antibody, as used herein, refers to one or more fragments of an antibody that retain the ability to specifically bind to an antigen (e.g., PA). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such molecules are encompassed within the term "antigen-binding portion" of an antibody. These antibody fragments are obtained using conventional techniques known to those with skill in the art, and the fragments are screened for binding in the same manner as are intact antibodies.

A "chimeric" protein comprises a first amino acid sequence linked to a second amino acid sequence with which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship.

The term "chimeric antibody", as used herein, refers to a molecule in which different portions are derived from different animal species, such as those having a variable region derived from a murine mAb and a human immunoglobulin constant region. (See, e.g., Cabilly et al., U.S. Pat. No. 4,816, 567; and Boss et al., U.S. Pat. No. 4,816,397, each of which is incorporated herein by reference in its entirety).

In one embodiment, an antibody of the invention is humanized. The term "humanized antibody", as used herein, refers to an antibody molecule from non-human species having one or more complementarity determining regions (CDRs) from the non-human species and a framework region from a human immunoglobulin molecule. (see e.g., U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. Nos. 4,816,567 and 5,225,539; European Patent Application 125,023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; Shaw et al., 1988, J. Natl. Cancer Inst. 80:1553-1559; Morrison 1985, Science 229:1202-1207; Oi et al., 1986, Bio/Techniques 4:214; Jones et al., 1986, Nature 321:552-525; Verhoeyan et al., 1988, Science 239:1534; and Beidler et al., 1988, J. Immunol. 141:4053-4060.

In another embodiment, an antibody of the invention is deimmunized. As used herein, the term "deimmunized antibody" refers to an antibody that is of a non-human origin but has been modified, i.e., with one or more amino acid substitutions, so that it is non-immunogenic or less immunogenic to a human when compared to the starting non-human antibody. In preferred embodiments, the deimmunized anti-anthrax antibody comprises one or more non-human $V_H$ or $V_L$ sequences modified to comprise one or more amino acid substitutions so that the deimmunized antibody is non-immunogenic or less immunogenic to a human when compared to the respective unmodified non-human sequences (see WO 00/34317, WO 98/52976, and WO2005/002529, all of which are incorporated herein by reference in their entirety).

As used herein the term "variable region CDR amino acid residues" includes amino acids in a CDR or complementarity determining region as identified using sequence or structure based methods. As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

| CDR Definitions | | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1] Residue numbering follows the nomenclature of Kabat et al., supra
[2] Residue numbering follows the nomenclature of Chothia et al., supra
[3] Residue numbering follows the nomenclature of MacCallum et al., supra As used herein the term "variable region framework (FR) amino acid residues" refers to those amino acids in the framework region of an Ig chain. The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable region and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light claim variable region CDRs. Similarly, using the definition of CDRs by Chothia et al. or McCallum et al. the framework region boundaries are separated by the respective CDR termini as described above. In preferred embodiments the CDRs are as defined by Kabat.

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen). The subject binding molecules have at least one binding site specific for PA of *Bacillus anthracis*.

With regard to the binding of an antibody to an antigen, the term "specific binding" or "specifically binds to" or is "specific for" a particular polypeptide or an epitope on a particular target means binding that is measurably different from a non-specific interaction. Preferably, any binding in the non-specific interaction is not substantially different from background. In one embodiment, the term "specific binding" refers to binding to a particular polypeptide or epitope on the molecule for which it is specific without substantial binding (e.g., exhibiting essentially background binding) to a molecule for which it is not specific. Specific binding can be measured, for example, by determining binding of a molecule compared to binding of a control molecule. Antibodies that exhibit "specific binding" or "specifically bind to" or are "specific for" a particular polypeptide or an epitope on a particular polypeptide target may have a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater.

In one embodiment, the polypeptides of the invention are modified antibodies. As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen).

In one embodiment, a binding molecule of the invention comprises a constant region, e.g., a heavy chain constant region, which is modified compared to a wild-type constant region. That is, the polypeptides of the invention disclosed herein may comprise alterations or modifications to one or more of the three heavy chain constant domains (CH1, CH2 or CH3) and/or to the light chain constant region domain (CL). Exemplary modifications include additions, deletions or substitutions of one or more amino acids in one or more domains.

As used herein, the term "neutralizing" with reference to antibodies includes antibody molecules or antigen binding fragments that bind to an antigen of a pathogenic agent, in its physiological form (e.g., a form which exists in an animal) and which, used alone, prevents or reduces infection or pathogenic effects of a pathogenic agent. In one embodiment, the neutralizing antibody binds to an eptiope of an infectious agent or a toxin which is in a form that is infectious or toxic to cells, e.g., mammalian cells. In one embodiment, the prevention of infection or pathogenic effects can be exhibited over the range of practically testable concentrations of the antibody in vivo or in vitro. In another embodiment, prevention of infection or pathogenic effects can be exhibited over the range of practically testable concentrations of the antibody or can be exhibited at low concentrations of the antibody.

In one embodiment, a neutralizing antibody binds to the protective antigen (PA) of *B. anthracis* (including native PA and recombinantly produced PA), wherein such binding prevents the physiological function of PA, i.e., facilitating the entry of the edema factor (EF) and the lethal factor (LF) into cells and causing pathogenic effects. The vegetative *B. anthracis* bacteria excrete a tripartite exotoxin, which consists of three polypeptides: protective antigen (PA, 83 kDa), lethal factor (LF, 90 kDa) and edema factor (OF, 89 kDa). The two components (OF and LF) of the toxin enzymatically modify substrates within the cytosol of the mammalian cells. OF is an adenylate cyclase that impairs the host defenses through a variety of mechanisms inhibiting phagocytosis and LF is a zinc dependent protease that cleaves several mitogen activated protein kinase kinases (MAPKK) and causes lysis of macrophages. To intoxicate mammalian cells, the third component of the toxin PA, binds to a ubiquitously expressed cellular receptor, Tumor Endothelium Marker-8 (TEM8).

II. Anti-Anthrax Antibodies

Preferred antibodies of the invention bind to epitopes of *Bacillus anthracis* toxin which can neutralize the effect of the toxin. In one embodiment, an antibody of the invention binds to lethal factor (LF). In another embodiment, an antibody of the invention binds to protective antigen (PA).

Antibodies for use in the compositions and methods of the invention may be known or may be made using methods well known in the art.

Exemplary antibodies may be obtained from natural sources or produced by hybridoma, recombinant or chemical synthetic methods, including modification of constant region functions by genetic engineering techniques (U.S. Pat. No. 5,624,821). An antibody of the present invention may be derived from a mammal and can be of any isotype.

An anti-anthrax mAb that specifically binds to anthrax toxin can be produced using techniques know to one of ordinary skill in the art. For example, a mammal can be immunized with, e.g., attenuated anthrax spores or purified molecules derived therefrom (or a highly homologous form of the molecule).

In one embodiment, an antibody of the invention binds to PA. The anthrax PA is the dominant antigen in both natural and vaccine-induced immunity to anthrax infection. It is also essential for host cell intoxication in combination with either lethal factor (LF) or edema factor (EF), producing lethal toxin or edema toxin, respectively. The anthrax "protective antigen" (PA) is an 83 kDa protein produced by *Bacillus anthracis*. PA is one of two protein components of the lethal or anthrax toxin produced by *B. anthracis*. The 83 kDa PA binds at its carboxyl-terminus to a cell surface receptor, where it is specifically cleaved by a protease, e.g., furin, clostripain, or trypsin. This enzymatic cleavage releases a 20 kDa amino-terminal PA fragment, while a 63 kDa carboxyl-terminal PA fragment remains bound to the cell surface receptor. The description of protective antigen includes binary toxin functional equivalents and other epitopes of interest, e.g., the a 63 kDa PA fragment that results from the enzymatic cleavage of the 83 kDa PA. Processed PA contains both a cell surface receptor binding site at its carboxyl-terminus and a lethal factor binding site at its new amino-terminus.

For example, the 14B7 anti-PA antibody was initially prepared by Little et al., in 1988 by immunizing female BALB/c mice with 2.5 ug-100 ug of purified protective antigen (PA) protein either intraperitoneally or intravenously at various time points. Spleen cells from immunized mice were then fused with logarithmically growing SP2/0-Ag14 myeloma cells, and hybridoma cultures were screened by the ELISA method to determine immunoglobulin subtype and subclass specificity. Positive hybridomas were subcloned twice by limiting dilution, and one to four clones for each hybridoma were expanded in vitro. Ascites from were produced by inoculating $1\times10^6$ hybridoma cells intraperitoneally (IP) into BALB/c female mice 2 to 8 weeks after IP injection of 0.5 ml of 2,6,10,14-tetramethyl pentadecane.

At an appropriate time after immunization of the mammal e.g., when the specific antibody titers are highest, antibody-producing cells can be obtained from the subject and used to prepare monoclonal antibodies by standard techniques, such as the hybridoma technique originally described by Kohler and Milstein (1975, Nature 256:495-497), the human B cell hybridoma technique by Kozbor et al. (1983, Immunol. Today 4:72), the EBV-hybridoma technique by Cole et al. (1985, Monoclonal Antibodies and Cancer Therapy, Alan R. Liss, Inc., pp. 77-96) or trioma techniques. The technology for producing hybridomas is well known (see Current Protocols in Immunology, 1994, John Wiley & Sons, Inc., New York, N.Y.). Hybridoma cells producing a monoclonal antibody of the invention are detected by screening the hybridoma culture supernatants for antibodies that anthrax toxin, e.g., using a standard ELISA.

In one embodiment, an antibody of the invention is monoclonal. Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. Monoclonal antibodies of the invention may also be made by recombinant DNA methods (U.S. Pat. No. 4,816,567).

In the hybridoma method of generating monoclonal antibodies, mammal, e.g., a mouse or a hamster, is immunized, e.g., described as hereinabove described to elicit lymphocytes that produce or are capable of producing antibodies that will bind to anthrax (see, e.g., U.S. Pat. No. 5,914,112, which is incorporated herein by reference in its entirety.)

Alternatively, lymphocytes may be immunized in vitro. Lymphocytes are then fused with myeloma cells using a suitable fusing agent, such as polyethylene glycol, to form a hybridoma cell (Goding, Monoclonal Antibodies: Principles and Practice, pp. 59 103, Academic Press, 1986). The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT deficient cells.

Preferred myeloma cells are those that fuse efficiently, support stable high level production of antibody by the selected antibody producing cells, and are sensitive to a medium such as HAT medium. Among these, preferred myeloma cell lines are murine myeloma lines, such as those derived from MOPC 21 and MPC 11 mouse tumors available from the Salk Institute Cell Distribution Center, San Diego, Calif. USA, and SP 2 cells available from the American Type Culture Collection, Rockville, Md. USA. Human myeloma and mouse-human heteromyeloma cell lines also have been described for the production of human monoclonal antibodies (Kozbor, 1984, J. Immunol., 133:3001; Brodeur et al., Monoclonal Antibody Production Techniques and Applications, pp. 51 63 (Marcel Dekker, Inc., New York, 1987)). Culture medium in which hybridoma cells are growing is assayed for production of monoclonal antibodies directed against the antigen.

Preferably, the binding specificity of monoclonal antibodies produced by hybridoma cells is determined by immunoprecipitation or by an in vitro binding assay, such as radioimmunoassay (RIA) or enzyme linked immuno-absorbent assay (ELISA). The binding affinity of the monoclonal antibody can, for example, be determined by the Scatchard analysis of Munson et al., 1980, Anal. Biochem., 107:220.

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59 103 (Academic Press, 1986)). Suitable culture media for this purpose include, for example, D-MEM or RPMI 1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A Sepharose, hydroxylapatite chromatography, gel electrophoresis, dialysis, or affinity chromatography.

Alternative to preparing monoclonal antibody-secreting hybridomas, an anti-anthrax antibody can be identified using other art recognized techniques, e.g., can be isolated by screening a recombinant combinatorial immunoglobulin library (e.g., an antibody phage display library), e.g., with anthrax toxin. Kits for generating and screening phage display libraries are commercially available (e.g., Pharmacia Recombinant Phage Antibody System, Catalog No. 27-9400-01; and the Stratagene antigen SurfZAP™ Phage Display Kit, Catalog No. 240612). Additionally, examples of methods and reagents particularly amenable for use in generating and screening antibody display library can be found in, for example, U.S. Pat. Nos. 5,223,409 and 5,514,548; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., 1991, Bio/Technology 9:1370-1372; Hay et al., 1992, Hum. Antibod. Hybridomas 3:81-85; Huse et al., 1989, Science 246:1275-1281; Griffiths et al., 1993, EMBO J. 12:725-734.

In other embodiments, nucleic acid molecules encoding the heavy and light chains of an anti-anthrax mAb, are prepared from the hybridoma cell line by standard methods known in the art. As a non-limiting example, cDNAs encoding the heavy and light chains of the anti-anthrax are prepared by priming mRNA using appropriate primers, followed by PCR amplification using appropriate forward and reverse primers. Commercially available kits for cDNA synthesis can be used. The nucleic acids are used in the construction of expression vector(s). The expression vector(s) are transfected into a suitable host. Non-limiting examples include E. coli, yeast, insect cell, and mammalian systems, such as a Chinese hamster ovary cell line. Antibody production can be induced by standard method known in the art.

In embodiments where non-human antibodies or antigen binding portions thereof are incorporated into a construct, the antibody or antigen binding portion thereof may be modified to reduce its immunogenicity in a human subject. For example, techniques developed for the production of "chimeric antibodies" (Morrison et al., 1984, Proc. Natl. Acad. Sci., 81, 6851-6855; Neuberger et al., 1984, Nature 312, 604-608; Takeda et al., 1985, Nature, 314, 452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, each of which is incorporated herein by reference in its entirety)

Humanized antibodies or antigen binding portions thereof can also be used in the constructs of the invention. Humanized antibodies are antibody molecules from non human species having one or more complementarity determining regions (CDRs) from the non human species and a framework region from a human immunoglobulin molecule. (see e.g., U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. Nos. 4,816,567 and 5,225,539; European Patent Application 125,023; Better et al., 1988, Science 240: 1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; Shaw et al., 1988, J. Natl. Cancer Inst. 80:1553-1559; Morrison 1985, Science 229:1202-1207; Oi et al., 1986, Bio/Techniques 4:214; Jones et al., 1986, Nature 321:552-525; Verhoeyan et al., 1988, Science 239: 1534; and Beidler et al., 1988, J. Immunol. 141:4053-4060.

Complementarity determining region (CDR) grafting is another method of humanizing antibodies. It involves reshaping murine antibodies in order to transfer full antigen specificity and binding affinity to a human framework (Winter et al. U.S. Pat. No. 5,225,539). CDR grafted antibodies have been successfully constructed against various antigens, for example, antibodies against IL 2 receptor as described in Queen et al., 1989 (Proc. Natl. Acad. Sci. USA 86:10029); antibodies against cell surface receptors CAMPATH as described in Riechmann et al. (1988, Nature, 332:323; antibodies against hepatitis B in Cole et al. (1991, Proc. Natl. Acad. Sci. USA 88:2869); as well as against viral antigens respiratory syncitial virus in Tempest et al. (1991, Bio Technology 9:267). CDR grafted antibodies are generated in which the CDRs of the murine monoclonal antibody are grafted into a human antibody. Following grafting, in one embodiment, additional amino acid changes in the framework region may be made to maintain affinity, presumably because framework residues are necessary to maintain CDR conformation, and some framework residues have been demonstrated to be part of the antigen binding site. However, in order to preserve the framework region so as not to introduce any antigenic site, the sequence is compared with established germline sequences followed by computer modeling.

A deimmunized antibody or antigen binding portion thereof can also be used in the present invention. As used herein, the term "deimmunized antibody" refers to an antibody that is of a non-human origin but has been modified, i.e., with one or more amino acid substitutions, so that it is non-immunogenic or less immunogenic to a human when compared to the starting non-human antibody. In preferred embodiments, the deimmunized anti-anthrax antibody comprises one or more non-human $V_H$ or $V_L$ sequences modified to comprise one or more amino acid substitutions so that the deimmunized antibody is non-immunogenic or less immunogenic to a human when compared to the respective unmodified non-human sequences (see WO 00/34317, WO 98/52976, and U.S. Provisional Application No. 60/458,869 filed on Mar. 28, 2003, all of which are incorporated herein by reference in their entirety).

Completely human antibodies are particularly desirable for therapeutic treatment of human patients. In one embodiment, fully human antibodies can be made using techniques that are known in the art. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make antibodies are described in U.S. Pat. Nos. 6,150,584; 6,458,592; 6,420,140.

The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, Int. Rev. Immunol. 13:65 93). For a detailed discussion of this technology for producing human antibodies and human monoclonal antibodies and protocols for producing such antibodies, see e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.; see, for example, U.S. Pat. No. 5,985,615) and Medarex, Inc. (Princeton, N.J.), can be engaged to provide human antibodies directed to anthrax using technology similar to that described above.

Completely human antibodies which recognize and bind a selected epitope can also be generated using a technique referred to as "guided selection." In this approach a selected non human monoclonal antibody, e.g., a mouse antibody, is used to guide the selection of a completely human antibody recognizing the same epitope (Jespers et al., 1994, Bio/technology 12:899-903).

Several neutralizing anti-anthrax antibodies are known in the art and can be used in the subject formulations. For example, the 14B7 antibody (the amino acid sequence of the CDRs and variable region of this antibody can be found, e.g., in Maynard et al. 2002. Nature Biotechnology 20:597). In this same reference, the CDR and variable region sequences for the variant antibodies A2E, Q55, 1H, and L87 can also be found. Additional exemplary antibodies include, e.g., the AVP-21D9 antibody (Peterson et al. 2006. Infect. Immun. 74:1016), the 7.5G and 10F4 antibodies (Rivera et al. 2006. Infect. Immun. 74:4149). Exemplary neutralizing anti-lethal factor antibodies against anthrax, e.g., the 5B13B1 and 3C16C3 antibodies (Lim et al. 2005. Infect. Immun. 73(10): 6547), the LF8 antibody (Zhao et al. 2003. Hum. Antibodies. 12(4):129), and an an anti-LF antibody (U.S. patent application Ser. No. 10/410,647) are also well known in the art and can be used in the formulations of the instant invention.

Antibodies can be produced using known methods, e.g., they may be made as ascites fluid or may be made in cell culture, e.g., by growing hybridoma cells or by transfecting cells with nucleic acid molecules encoding the antibody (e.g., bacterial or eukaryotic cells). In a preferred embodiment, the antibodies of the invention are glycosylated, although non-glycosylated antibodies may also be used.

In one embodiment, a full-length antibody may be used in a composition or method of the invention. In another embodiment, an antibody that binds to anthrax does not comprise an Fc domain. For example, the constructs of the invention can comprise antigen binding fragments. Such fragments may be recombinantly produced and engineered, synthesized, or produced by digesting an anti-anthrax antibody with a proteolytic enzyme.

In one embodiment, the term "antibody" as used herein includes fragments of antibodies, i.e., antigen binding portions of antibodies produced by the modification of whole antibodies or synthesized de novo. Exemplary portions include an Fab, an Fab', an (Fab')2, or an Fv fragment of an immunoglobulin molecule. Such an Fab, Fab' or Fv fragment can be obtained, e.g., from a full antibody by enzymatic processing. For example, pepsin digests an antibody below the disulfide linkages in the hinge region to produce an $(Fab')_2$ fragment of the antibody which is a dimer of the Fab composed of a light chain joined to a VH-CH1 by a disulfide bond. The $(Fab')_2$ fragments may be reduced under mild conditions to reduce the disulfide linkage in the hinge region thereby converting the $(Fab')_2$ dimer to a Fab' monomer. The Fab' monomer is essentially an Fab with part of the hinge region. See Paul, ed., 1993, Fundamental Immunology, Third Edition (New York: Raven Press), for a detailed description of epitopes, antibodies and antibody fragments. One of skill in the art will recognize that such Fab' fragments may be synthesized de novo either chemically or using recombinant DNA technology.

Alternatively, such a fragment can be obtained from a phage display library by affinity screening and subsequent recombinant expressing (see, e.g., Watkins et al., Vox Sanguinis 78:72-79; U.S. Pat. Nos. 5,223,409 and 5,514,548; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., 1991, Bio/Technology 9:1370-1372; Hay et al., 1992, Hum. Antibod. Hybridomas 3:81-85; Huse et al., 1989, Science 246:1275-1281; Griffiths et al., 1993, EMBO J. 12:725-734; and McCafferty et al., 1990, Nature 348:552 554, each of which is incorporated herein by reference in its entirety).

Yet another alternative is to use a "single chain" Fv fragment. Single-chain Fv (scFv) fragments can be constructed in a variety of ways. Although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). For example, the C-terminus of $V_H$ can be linked to the N-terminus of $V_L$. Typically, a linker (e.g., $(GGGGS)_4$ (SEQ ID NO: 3)) is placed between $V_H$ and $V_L$. However, the order in which the chains can be linked can be reversed, and tags that facilitate detection or purification (e.g., Myc-, His-, or FLAG-tags) can be included (tags such as these can be appended to any anti-anthrax antibody or antibody fragment of the constructs of the invention; their use is not restricted to scFv). For a review of scFv see Pluckthun in The Pharmacology of Monoclonal Antibodies, vol. 113, 269-315 (Rosenburg and Moore eds., Springer-Verlag, New York 1994).

In another preferred embodiment, a single chain Fv (scFv) fragment can be obtained, e.g., from a library of phage-displayed antibody fragments by affinity screening and subsequent recombinant expression.

In still another embodiment, the antigen-binding portion of the construct molecule is a single-chain antibody (scAb). As used herein, a single-chain antibody (scAb) includes antibody fragments consisting of an scFv fused with a constant domain, e.g., the constant κ domain, of an immunoglobulin molecule. In another embodiment, the antigen-binding portion of the construct molecule is a Fab, Fab', $(Fab')_2$, Fv, scFv, or scAb fragment fused with a linker peptide of a desired length comprising a chosen amino acid sequence. In preferred embodiment, the linker peptide consists of 1, 2, 5, 10, or 20 amino acids. Exemplary linker peptides are known in the art.

In alternative embodiments, antibodies of the present invention can be heavy chain dimers or light chain dimers. Still further, an anti-anthrax antibody light or heavy chain, or portions thereof, for example, a single domain anti-anthrax antibody (DAb), can be used.

Also included in the term antibody fragments are diabodies. The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., 1993 Proc. Natl. Acad. Sci. USA 90: 6444-8.

In one embodiment, the antibodies bind to their target with high affinity. In one embodiment, an isolated antibody or fragment thereof may bind to Bacillus anthracis protective antigen with an affinity $K_d$ of between about 2.3 nM and about 12 nM as determined by surface plasmon resonance. Such an antibody or fragment thereof may be further defined as binding immunologically to Bacillus anthracis protective antigen with a binding affinity $K_d$ of between about 2 nM and about 5 nM, between about 5 nM and about 10 nM, and/or between about 10 nM and about 15 nM.

In one embodiment, the binding molecules of the invention comprise or are derived from at least one humanized or deimmunized antibody variable region, e.g., a light chain or heavy chain variable region.

The term "humanized antibody" refers to an antibody comprising at least one chain comprising variable region framework residues substantially from a human antibody chain (referred to as the "acceptor antibody") and at least one complementarity determining region ("CDR") substantially from a non-human antibody, (referred to as the "donor antibody"). The constant region(s), if present, are also substantially or entirely from a human immunoglobulin.

The CDRs of murine 14B7 are set forth below in Table 1:

TABLE 1

14B7 CDR Sequences

| CDR L1 | RASQDIRNYLN | SEQ ID NO: 4 |
|---|---|---|
| CDR L2 | YTSRLQS | SEQ ID NO: 5 |
| CDR L3 | QQGNTLPWT | SEQ ID NO: 6 |
| CDR H1 | YAFSSSWMN | SEQ ID NO: 7 |
| CDR H2 | RIYPGDGDTNYNGKFKG | SEQ ID NO: 8 |
| CDR H3 | SGLLRYAMDY | SEQ ID NO: 9 |

In one embodiment, an antigen binding molecule of the invention comprises at least one heavy or light chain CDR of a 14B7 antibody molecule as set forth in Table 1. In another embodiment, an antigen binding molecule of the invention comprises at least two CDRs a 14B7 antibody molecule. In another embodiment, an antigen binding molecule of the invention comprises at least three CDRs from a 14B7 antibody molecule. In another embodiment, an antigen binding molecule of the invention comprises at least four CDRs from a 14B7 antibody molecule. In another embodiment, an antigen binding molecule of the invention comprises at least five CDRs from a 14B7 antibody molecule. In another embodiment, an antigen binding molecule of the invention comprises at least six CDRs from a 14B7 antibody molecule. In one embodiment, the at least one CDR (or at least one CDR from the greater than one 14B7 CDRs that are present in the binding molecule) is modified to vary in sequence from the CDR of a naturally occurring 14B7 molecule, yet retains the ability to bind to PA. For example, in one embodiment, the sequence of CDRL2 is YTSRLLP (SEQ ID NO: 10). In another embodiment, the sequence of CDRH2 is RIYPGDGDTNYNGKFQG (SEQ ID NO: 11).

In one embodiment, a binding molecule of the invention comprises three 14B7 light chain CDRs (CDRL1, CDRL2, and CDRL3) or a variant form thereof and a human light chain framework region. In one embodiment, a binding molecule of the invention further comprises a least one alteration of the human framework region, e.g., a backmutation to the corresponding murine residue at that position (using known methodology) or other mutation which may enhance, e.g., the affinity or stability of the molecule. For example, in one embodiment the FR4 region of the light chain comprises the amino acid sequence FGGGTKLEIRR (SEQ ID NO: 12) or FGGGTKLEIKR (SEQ ID NO: 13).

In one embodiment, a binding molecule of the invention comprises three 14B7 heavy chain CDRs (CDRH1, CDRH2, and CDRH3) or a variant form thereof and a human heavy chain framework region. In one embodiment, a binding molecule of the invention further comprises a least one alteration of the human framework region, e.g., a backmutation to the corresponding murine residue at that position. It will be understood that combinations of these light and heavy chain CDRs are also within the scope of the invention, for example, 3 light chain CDRs and 3 heavy chain CDRs derived from 14B7, or variants thereof, can be combined to form a binding molecule comprising 6 CDRs.

In one embodiment, a binding molecule of the invention comprises three 14B7 light chain CDRs (CDRL1, CDRL2, and CDRL3) or a variant form thereof and a framework region. In one embodiment, a binding molecule of the invention further comprises a least one alteration of the framework region which decreases the immunogenicity of the molecule.

In one embodiment, a binding molecule of the invention comprises three 14B7 heavy chain CDRs (CDRH1, CDRH2, and CDRH3) or a variant form thereof and a heavy chain framework region. In one embodiment, a binding molecule of the invention further comprises a least one alteration of the framework region which decreases the immunogenicity of the molecule. It will be understood that combinations of these light and heavy chain CDRs are also within the scope of the invention, for example, 3 light chain CDRs and 3 heavy chain CDRs derived from 14B7, or variants thereof, can be combined to form a binding molecule comprising 6 CDRs.

Figure 5:
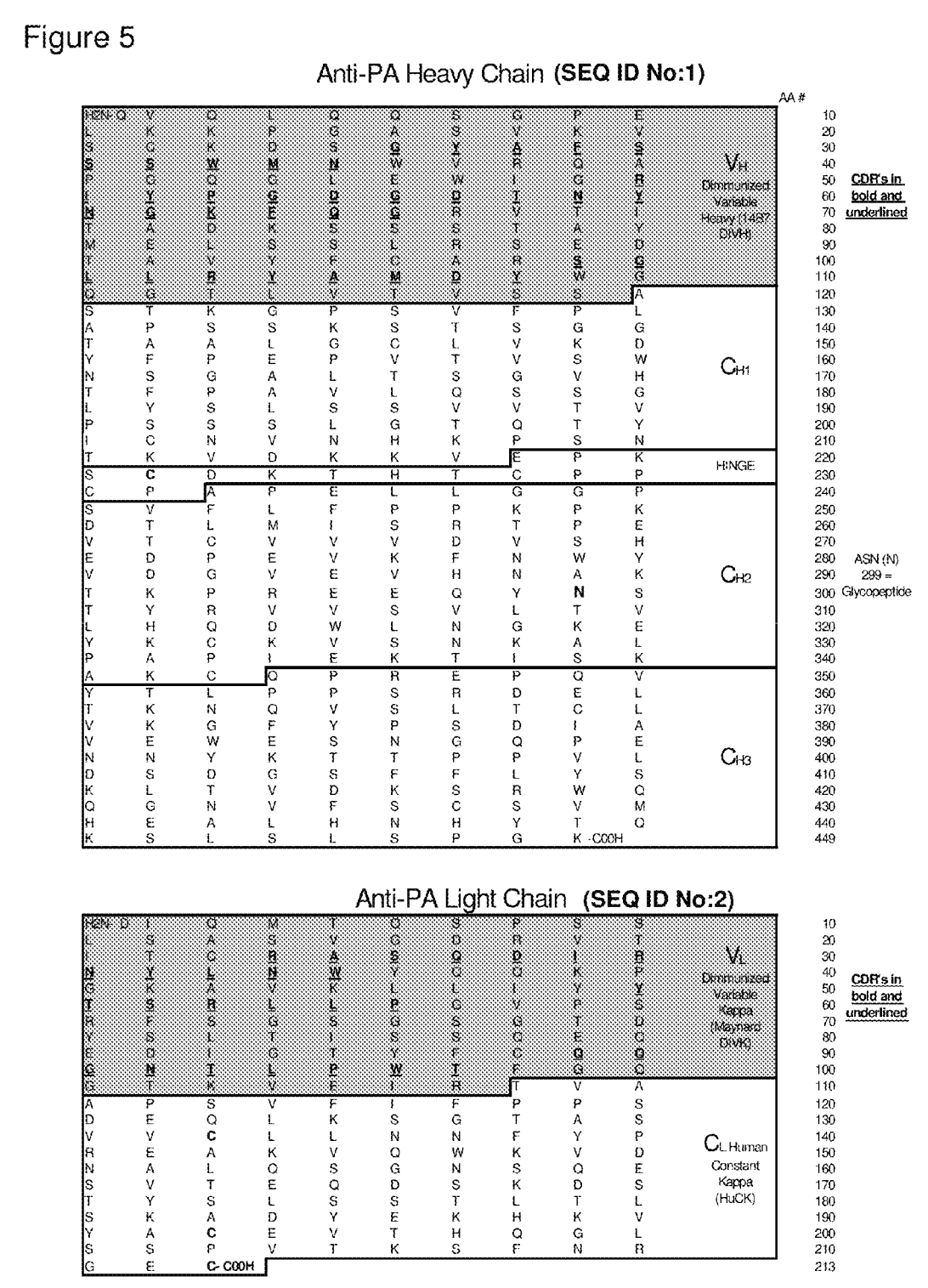

In one embodiment, a binding molecule of the invention comprises the light chain CDRs shown in FIG. 5. In another embodiment, CDRL2 comprises the sequence YTSRLQS (SEQ ID NO: 5), YTSRLQP (SEQ ID NO: 14), YTSRLAS (SEQ ID NO: 15), or YTSRLLP (SEQ ID NO: 10).

In another embodiment, a binding molecule of the invention comprises the heavy chain CDRs shown in FIG. 5. In another embodiment, CDRH3 comprises the sequence SGALRYAMDY (SEQ ID NO: 16).

In one embodiment, a binding molecule of the invention comprises a light chain variable region sequence shown in FIG. 5.

In one embodiment, a binding molecule of the invention comprises a heavy chain variable region sequence shown in FIG. 5.

In one embodiment, a binding molecule of the invention comprises both a heavy chain variable region sequence and a light chain variable region sequence shown in FIG. 5.

In one embodiment, a binding molecule of the invention comprises the amino acid sequence shown in FIG. 5.

III. Pharmaceutical Formulation

The formulations of the invention include at least one neutralizing anti-PA antibody in a pharmaceutically acceptable carrier. A "pharmaceutically acceptable carrier" refers to at least one component of a pharmaceutical preparation that is normally used for administration of active ingredients. As such, a carrier may contain any pharmaceutical excipient used in the art and any form of vehicle for administration. The compositions may be, for example, injectable solutions, aqueous suspensions or solutions, non-aqueous suspensions or solutions, solid and liquid oral formulations, salves, gels, ointments, intradermal patches, creams, lotions, tablets, capsules, sustained release formulations, and the like. Additional excipients may include, for example, colorants, taste-masking agents, solubility aids, suspension agents, compressing agents, enteric coatings, sustained release aids, and the like.

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa. (1980)). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In one embodiment, the present invention provides a stabilized formulation including a neutralizing anti-PA antibody, a tonicity agent, wherein the tonicity agent is present in an amount sufficient to render the formulation suitable for intramuscular infusion, and an amino acid or derivative thereof, where the amino acid or derivative thereof is present in an amount sufficient to maintain a physiologically suitable pH. In an exemplary embodiment, the tonicity agent is sorbitol. In another exemplary embodiment, the amino acid is histidine.

In exemplary embodiments of the invention, the neutralizing anti-PA antibody is present from about 100 mg/ml to about 300 mg/ml. In exemplary embodiments of the present invention, the neutralizing anti-PA antibody is present from about 100 mg/ml to about 200 mg/ml. In other exemplary embodiments of the present invention, the neutralizing anti-PA antibody is present from about 100 mg/ml to about 140 mg/ml. In other exemplary embodiments, formulations of the present invention include neutralizing anti-PA antibody at about 140 mg/ml. In yet other exemplary embodiments, formulations of the present invention include neutralizing anti-PA antibody at about 120 mg/ml. In further exemplary embodiments, formulations of the invention include neutralizing anti-PA antibody at about 100 mg/ml.

In one embodiment of the present invention, a formulation according to the present invention includes a neutralizing anti-PA antibody, sorbitol and histidine.

In some embodiments of the present invention, formulations of the present invention include sorbitol in an amount sufficient to maintain isotonicity of the formulation. In exemplary embodiments of the present invention, sorbitol is present from about 100 mM to about 300 mM. In other exemplary embodiments of the present invention, sorbitol is present at about 200 mM. In yet other exemplary embodiments, sorbitol is present at about 250 mM. In further exemplary embodiments, sorbitol is present at about 150 mM.

In some embodiments of the present invention, formulations of the present invention include histidine in an amount sufficient to maintain a physiologically suitable pH. In exemplary embodiments of the present invention, histidine is present from about 1 mM to about 100 mM. In other exemplary embodiments, histidine is present at about 40 mM.

In some embodiments of the invention, the formulation further includes a stabilizer. In exemplary embodiments of the present invention, the stabilizer is polysorbate 80. In some embodiments, the polysorbate 80 is present from about 0.001% w/v to about 0.1% w/v. In other embodiments, the polysorbate 80 is present at about 0.005% w/v. In preferred embodiments of the present invention, the polysorbate 80 is present at about 0.01% w/v.

In some embodiments of the invention, the formulation has a pH of about 5 to about 7. In exemplary embodiments of the present invention, the formulation has a pH of about 5.5. In another exemplary embodiment, the formulation has a pH of about 6.0. In yet another exemplary embodiment, the formulation has a pH of about 6.2. In further exemplary embodiments, the formulation has a pH of about 6.5.

In some embodiments, the formulation is stable to freezing. In other embodiments of the present invention, the formulation is suitable for intravenous administration. In an exemplary embodiment of the present invention, the formulation is suitable for intramuscular administration. In another embodiment, the formulation is suitable for intravenous or subcutaneous administration.

In other embodiments, the formulation is substantially free of preservatives.

In some embodiments of the present invention, the formulation is stable for at least about 12 months. In some embodiments, the formulation is stable for at least about 18 months. In some embodiments of the present invention, the formulation is stable for at least about 24 months. In some embodiments of the present invention, the formulation is stable for at least about 30 months.

In exemplary embodiments of the present invention, the formulation is stable from about −80° C. to about 40° C. In some exemplary embodiments, the formulation is stable from about 0° C. to about 25° C. Preferably, the formulation is stable from about 2° C. to about 8° C.

In a preferred embodiment of the present invention, a formulation includes about 140 mg/mL neutralizing anti-PA antibody, about 40 mM histidine, about 200 mM sorbitol, and has a pH of about 5.5. In one embodiment, this formulation can be diluted to a concentration suitable for intramuscular administration of the neutralizing anti-PA antibody at 100 mg/mL. In a particular embodiment, a formulation suitable for intramuscular administration includes about 100 mg/mL neutralizing anti-PA antibody, about 40 mM histidine, about 200 mM sorbitol and has a pH of about 5.5.

Antibodies can also be administered in the form of a depot injection or implant preparation, which can be formulated in such a manner as to permit a sustained release of the active ingredient. In one embodiment, a composition comprises monoclonal antibody at 5 mg/mL, formulated in aqueous buffer consisting of 50 mM L-histidine, 150 mM NaCl, adjusted to pH 6.0 with HCl.

In a preferred embodiment, a composition of the invention comprises certain inactive components. For example, in one embodiment, the inactive components of the formulation are as shown in Table 1 and include the salts which form the phosphate buffered saline solution (pH 7.4). This formulation optionally includes the presence of Tween 80 (Polysorbate 80) to maintain product solubility and stability.

TABLE 1

Excipients

| Component | Final concentration (per mL) |
|---|---|
| Sodium Phosphate Dibasic | 42 mM |
| Sodium Phosphate Monobasic | 8 mM |
| Sodium Chloride | 150 mM |
| WFI | N/A |
| Tween 80* (optional) | 0.01% |
| pH | 7.4 |
| Total Volume | 1.5 mL |

In one embodiment, the anti-anthrax antibody content in the buffered solution is 12.5 mg/ml. Using this formulation, 1.5 ml can be administered IV for a dose of 18 mg or 3.0 ml can be administered IM for a dose of 38 mg anti-PA antibody. In another embodiment, the anti-anthrax content of a composition of the invention is greater than 12.5 mg/ml.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249: 1527 (1990) and Hanes, *Advanced Drug Delivery Reviews* 28:97 (1997)).

The pharmaceutical compositions can be included in a kit, in a container, pack, or dispenser together with instructions for administration.

IV. Dose of Antibodies

Effective doses of the compositions of the present invention, for the prophylactic or therapeutic treatment of anthrax vary depending upon many different factors, including means of administration, site of administration, physiological state of the subject, other medications administered (e.g., an antibiotic(s) or vaccine(s)), and whether treatment is prophylactic or therapeutic. Usually, the subject is a human but non-human mammals (including transgenic mammals) can also be treated.

The dosage and frequency of administration can vary depending on whether the treatment is prophylactic or therapeutic. In prophylactic applications, compositions containing the present antibodies or a cocktail thereof are administered to a subject not already in the disease state to enhance the subject's resistance. Such an amount is defined to be a "prophylactic effective dose." In this use, the precise amounts again depend upon the subject's state of health and general immunity, but generally range from at least about 15 to at least about 150 mg per dose. In one embodiment a dose of at least about 120 mg may be given.

The subject antibodies can be administered via any route, with IV, IM, and subcutaneous being preferred.

In one embodiment, for IV dosing, a dose of at least about 10 may be administered. In another embodiment, a dose of at least about 15 mg may be administered to a subject. In another embodiment, a dose of at least about 18 mg may be administered to a subject.

For example, of IM dosing, a dose of at least about 25 mg may be administered to a subject. In another embodiment, a dose of at least about 30 mg may be administered to a subject. In another embodiment, a dose of at least about 35 mg may be administered to a subject. In another embodiment, a dose of at least about 38 mg may be administered to a subject. In another embodiment, a dose of at least about 40 mg may be administered to a subject. In another embodiment, a dose of at least about 45 mg may be administered to a subject. In another embodiment, a dose of at least about 50 mg may be administered to a subject.

In one embodiment the dose of antibody is sufficient to obtain an initial average blood level of at least about 30-55 ug/ml. In another embodiment the initial average blood level is at least about 45-55 ug/ml.

V. Methods of Treatment

Therapeutic agents can be administered by intramuscular, intraveneous, subcutaneous, parenteral, topical, oral, intraarterial, intracranial, intraperitoneal, orintranasal means for prophylactic and/or therapeutic treatment. The most typical routes of administration of a protein drug is intravascular, subcutaneous, or intramuscular. Compositions of the invention can also be administered via the respiratory tract, e.g., using a dry powder inhalation device.

Agents of the invention can optionally be administered in combination with other agents that are at least partly effective in treatment of anthrax, e.g., antibiotics.

In prophylactic applications, pharmaceutical compositions or medicaments are administered to a patient in order to prevent the development of inhalation anthrax in a human subject either prior or after exposure to *B. anthracis* spores in an amount sufficient to eliminate or reduce the risk, lessen the severity, or delay the outset of the disease, its complications and intermediate pathological phenotypes presenting during development of the disease. In therapeutic applications, compositions or medicaments are administered to a subject suspected of, or already suffering from inhalation anthrax after exposure to *B. anthracis* spores in an amount sufficient to cure, or at least partially arrest, the symptoms of the disease (biochemical, histologic and/or behavioral), including its complications and intermediate pathological phenotypes in development of the disease.

In some methods, administration of an antibody of the invention reduces or eliminates the disease. An amount adequate to accomplish therapeutic or prophylactic treatment is defined as a therapeutically- or prophylactically-effective dose. In both prophylactic and therapeutic regimes, agents can be administered in one or in several dosages until a sufficient response has been achieved.

For prophylactic immunization with an antibody, exemplary dosage ranges from about 1-400 mg per patient. For example, dosages can be 10 to 300 mg or 20 to 200 mg when administered. Exemplary dosages for IV administration are about 10-30 mg and for IM administration are about 20 to 50 mg. Subjects can be administered such doses once or on multiple occasions. For example, such doses can be administered daily, on alternative days, weekly or according to any other schedule determined by one of ordinary skill in the art, e.g., by empirical analysis.

For therapeutic administration, an exemplary treatment entails administration of one dosed within 3 to 36 hours of exposure to anthrax spores. In one embodiment, additional doses may be administered. Additional exemplary treatment regimes entail administration at 5, 8, 12, 18, 24, or 36 hours after exposure to anthrax spores. In one embodiment, additional doses may be administered.

Alternatively, antibody can be administered as a sustained release formulation, in which case less frequent administration is required. Dosage and frequency vary depending on the half-life of the antibody in the subject. In general, human antibodies show the longest half-life, followed by humanized antibodies, chimeric antibodies, and nonhuman antibodies.

Combination with Additional Agents

In one embodiment, of the invention, the subject antibodies are administered in combination with one or more antibiotics. In one embodiment, the one or more antibiotic is selected from the group consisting of doxycycline, amoxicillin, and a fluoroquinalone. In one embodiment the fluoroquinalone is selected from the group consisting of: ciprofloxacin, ofloxacin and levofloxacin. In one embodiment, the antibiotic can be administered at a lower dose and/or for a shorter period of time than it is normally administered.

In another embodiment, the subject antibodies are administered in combination with an anthrax vaccine (e.g., BioThraxT, formerly known as AVA) and, optionally, antibiotics.

VI. Kits

If desired, a kit incorporating an antibody or other agent useful in a method of the invention can be prepared. Such a kit can contain, in addition to the agent, a pharmaceutical composition in which the agent can be reconstituted for administration to a subject. The invention also provides kits containing the antibody formulations, or components necessary to make the antibody formulations, of the invention. The invention may also provide kits containing an antibiotic (e.g., fluoroquinolones including levofloxacin and/or ciprofloxacin), which can be used in combination with the anti-anthrax antibody formulations.

REFERENCES

Brookmeyer, R. E., Johnson, E. Barry, S. (2005) Modeling the incubation period of anthrax. Statistics in Medicine. 24:531-42

Cieslak T J, Eitzen E M. (1999) Clinical and epidemiologic principles of anthrax. Emerg Infect Dis. 5(4):552-555.

Comer J E, Chopra A K, Peterson J W, Konig R. (2005) Direct inhibition of T-lymphocyte activation by anthrax toxins in vivo. Infect Immun. 73(12):8275-81.

Dixon T C, Meselson M, Guillemin J, Hanna P C. (1999) Anthrax. N Engl J Med. 341(11):815-826.

During R L, Li W, Hao B, Koenig J M, Stephens D S, Quinn C P, Southwick F S. (2005) Anthrax lethal toxin paralyzes neutrophil actin-based motility. J Infect Dis. 192(5):837-45.

Erwin J L, DaSilva L M, Bavari S, et al. (2001) Macrophage-derived cell lines do not express proinflammatory cytokines after exposure to *Bacillus anthracis* lethal toxin. Infect Immun. 69(2):1175-7.

Fang H, Xu L, Chen T Y, et al. (2006) Anthrax lethal toxin has direct and potent inhibitory effects on B cell proliferation and immunoglobulin production. J Immunol. 176(10):6155-61.

Holty J E, Bravata D M, Liu H, et al. (2006) Systematic review: a century of inhalational anthrax cases from 1900 to 2005. Ann Intern Med. 144(4):270-80.

Jernigan J A, Stephens D S, Ashford D A, et al. (2001) Bioterrorism-related inhalational anthrax: the first 10 cases reported in the United States. Emerg Infect Dis. 7(6):933-944.

O'Brien J, Friedlander A, Dreier T, et al. (1985) Effects of anthrax toxin components on human neutrophils. Infect Immun. 47(1):306-10.

This invention is further illustrated by the following examples which should not be construed as limiting. The contents of all references, patents and published patent applications cited throughout this application are hereby incorporated by reference.

EXAMPLES

The following examples demonstrate that, after exposure to anthrax spores, the intramuscular (IM) administration of the claimed high-affinity anti-Protective Antigen (anti-PA) monoclonal antibody provides complete protection, and that the bioavailability of the claimed antibody by the IM route is similar to that of the intravascular (IV) route. Furthermore, the following examples also demonstrate that the co-administration of an anti-anthrax antibody to Protective Antigen and an antibiotic result in greater survival than antibiotic alone.

Example 1

Generation of the High-Affinity Anti-Protective Antigen Monoclonal Antibody

A deimmunized anti-PA MAb, a recombinant human immunoglobulin (IgG$_1$), is a basic four chain glycosylated protein consisting of two light chains and two glycosylated heavy chains produced from the NS0 mammalian cell culture. The molecular weight of the anti-PA antibody is 148.6 kDa, as determined by MALDI-TOF, and it has an isoelectric point of 9.6. Amino Acid Analysis (AA) of the anti-PA antibody agrees with the composition predicted from DNA sequencing and codon analysis. N-terminal sequencing of the heavy and light chains, which yielded 35 residues including the first complementarity determining region (CDR) of both chains, also agrees with the predicted amino acid sequence. Additional characterizations of reference standard material included peptide mapping, disulfide linkage analysis and carbohydrate analysis.

The anti-PA antibody is an affinity-enhanced deimmunized MAb to Protective Antigen (PA) of *Bacillus anthracis*. FIG. 1 provides an overview of the method for generating the high-affinity anti-PA antibody. The progenitor of the anti-PA antibody was murine anti-PA MAb 14B7, developed by investigators at USAMRIID and the NIH (Little et al., 1988). The mouse variable (V) regions of MAb 14B7 were affinity-enhanced (Maynard et al. 2002). The affinity-enhanced V regions were re-engineered into a chimeric MAb with human gamma 1 (IgH) and Kappa (IgL) constant regions, followed by further modifications to the variable regions to minimize immunogenic potential.

Manufacturing Process for the High-Affinity Anti-PA Monoclonal Antibody

The anti-PA antibody is produced in a high-productivity re-engineered NS0 cell line for manufacturing of product for advanced pharmaceutical development and stockpiling. A GMP Master Cell Bank has been generated, and upstream bioreactor and downstream purification method optimization have been completed. The cell line has been adapted to growth in serum-free medium, eliminating the need for animal products in the manufacturing process.

Briefly, a GMP clinical lot of the anti-PA antibody was produced by fed batch culture in a 2000 L bioreactor. The MAb was captured using protein A affinity chromatography and further purified using ion exchange chromatography. The purified MAb was subjected to concentration by diafiltration and sterile filtered. The ability of the process to clear adventitious viruses was validated, and the vialed product was a sterile liquid formulation in phosphate buffered saline at 12.6 mg/mL in stoppered glass vials stored at 2-8° C.

Example 2

Rabbit Spore Challenge Model Post-Exposure with or without Antibiotics

The rabbit spore challenge model was utilized to demonstrate that post-exposure administration of anti-PA leads to increased survival above that of levofloxacin (a fluoroquinolone antibiotic similar to ciprofloxacin but better-tolerated by rabbits) after an aerosolized *B. anthracis* (Ames strain) spore challenge. Levofloxacin is currently approved for preventing the development of inhalation anthrax. The IM dose selected (20 mg/rabbit) was twice that of the IV dose (10 mg/rabbit) of anti-PA to achieve comparable blood levels (Mohamed et al. 2005).

Aerosol Procedures:

Aqueous suspensions of *B. anthracis* (Ames strain) spores (MREF Lot B24) were aerosolized by a 3-jet Collison nebulizer and delivered to rabbits via a muzzle-only inhalation system. The target inhaled dose for the rabbit challenges was 200 Ames $LD_{50}$'s. The confirmed average challenge dose was somewhat higher (268 $LD_{50}$'s) The published aerosol Ames $LD_{50}$ value (Zaucha et al. 1998) for *B. anthracis* (Ames strain) spores in rabbits ($1.05 \times 10^5$ colony forming units) was used.

Treatment Groups:

Fifty-seven New Zealand White (NZW) rabbits (male and female) weighing between 2.0 and 3.0 kg were placed on study. Rabbits were divided into 5 groups of 9 (Groups 1, 3, 4, 5, 6) and one group of 12 (Group 2). Anthrax challenges were divided over three days with equal number of animals from each group challenged each day. All rabbits were aerosol challenged on Study Day 0. Study events for each animal were performed on the planned Study Day based on its assigned day of challenge.

Anti-PA (12.61 mg/mL) and anti-PA control (PBS) were administered approximately 9 hours (±3 hours) after anthrax challenge with the animals receiving either anti-PA or PBS (anti-PA Control) according to their group designation. Rabbits in Group 3 and Group 4 received a single 10 mg dose of anti-PA administered IV. Rabbits in Group 5 and Group 6 received a single 20 mg dose of anti-PA administered IM (10 mg in each hind leg). Rabbits in Group 1 and Group 2 received a single dose of PBS (anti-PA Control) administered IV at the same volume as the anti-PA IV treatment. anti-PA and PBS (anti-PA Control) treatments were not based on animal weight.

Levaquin® (Levo; 25 mg/mL) and Levaquin® control was administered approximately 9 hours (±3 hours) after anthrax challenge with the animals receiving Levo or Levo Control according to their group designation (Table 2-2). Once a day (sid) Levo and Levo Control dosing occurred at approximately 24 hour intervals (24±3 hours) until completed (a total of 5 oral doses administered). Rabbits in Group 2, Group 4 and Group 6 were administered approximately 50 mg/kg of Levo via oral gavage sid while rabbits in Group 1, Group 3 and Group 5 (Levo Control) were administered sterile water for injection via oral gavage with volumes comparable to the Levo groups (approximately 2.0 mL/kg of body weight). Levo and Levo Control dose volumes were based on Study Day—1 weight.

TABLE 1

Anti-PA and Levaquin ® Dosing Regimen

| | | Antibody and Control | | Antibiotic and Control | |
|---|---|---|---|---|---|
| Group | Rabbits per Group | anti-PA | PBS (anti-PA Control, IV) | Levo (50 mg/kg sid for 5 days, oral gavage) | Sterile Water (Levo Control, sid for 5 days, oral gavage) |
| 1 | 9 | − | + | − | + |
| 2 | 12 | − | + | + | − |
| 3 | 9 | 10 mg IV | − | − | + |
| 4 | 9 | 10 mg IV | − | + | − |
| 5 | 9 | 20 mg IM | − | − | + |
| 6 | 9 | 20 mg IM | − | + | − |

Sample sizes of nine (9) control and nine (9) or twelve (12) treated animals were calculated to be sufficient to provide greater than 80 percent power to detect a difference when the survival probabilities are 10 percent in the control group, 30% in the levofloxacin control group, and 80 percent in the treated groups, using a one-sided Fisher's exact test. A time-to-death analysis was performed on these data using Fisher's exact test to determine if there were differences in protection for the different groups based on a length of survival model. Log rank tests were used to determine if there were significant differences between the groups and if so, which groups are different.

Rabbits were observed twice each day during the quarantine period and prior to the start of the study. After anthrax challenge, surviving rabbits were observed twice daily for 34 days for clinical signs of illness and mortality due to anthrax infection. Rabbits that were moribund were euthanized. Gross necropsies were performed on rabbits found dead or moribund euthanized to confirm death or illness due to anthrax infection. At a minimum, brain, liver, spleen, kidney, lung, mediastinal lymph node and gross lesions were collected and placed into 10 percent neutral buffered formalin. Histopathology was performed on selected tissues when needed to confirm death by anthrax. Deaths or euthanasia were recorded at the time observed.

Survival data, average time to death±standard deviation, and the range are summarized in Table 2.

TABLE 2

Survival Data by Treatment Group

| Group | Description | Group Size | Number of Survivors | Number of Dead | Time to Death (Days) Average | Standard Deviation | Range |
|---|---|---|---|---|---|---|---|
| 1 | Process control | 9 | 0 | 9 | 3.6 | 1.0 | 2.4-4.9 |
| 2 | Levofloxacin only | 12 | 4 | 8 | 14.3 | 3.0 | 11.8-20.9 |
| 3 | ETI-204 IV | 9 | 9 | 0 | NA | NA | NA |
| 4 | ETI-204 IV plus Levo | 9 | 8 | 1 | NA[1] | NA | NA |
| 5 | ETI-204 IM | 9 | 9 | 0 | NA | NA | NA |
| 6 | ETI-204 IM plus Levo | 9 | 9 | 0 | NA | NA | NA |

[1] The single death in Group 4 occurred at 16.8 days (average and standard deviation not computable).

TABLE 3

Incidence of Positive *B. anthracis* culture in NZW Rabbits Following Aerosolized *B. anthracis* Challenge

| Group | Group Size | Blood Sample *B. anthracis* positive culture Moribund euthanized or found dead | Blood Sample *B. anthracis* positive culture Study Day 34 (end of study) | Tissue (spleen) Sample *B. anthracis* positive culture Moribund euthanized or found dead | Tissue (spleen) Sample *B. anthracis* positive culture Study Day 34 (end of study) |
|---|---|---|---|---|---|
| 1 | 9 | 8/9 | NA | 7/9 | NA |
| 2 | 12 | 8/8 | 0/4 | 7/8 | 0/4 |
| 3 | 9 | NA | 0/4 | NA | 0/4 |
| 4 | 9 | 1/1 | 0/4 | 1/1 | 0/4 |
| 5 | 9 | NA | 0/4 | NA | 0/4 |
| 6 | 9 | NA | 0/4 | NA | 0/4 |

Blood samples were collected into EDTA tubes to determine the presence or absence of *B. anthracis* in moribund rabbits, rabbits found dead, and from the survivors on the last Study Day. Blood was cultured to determine the presence or absence of bacteremia. Spleen tissue was also cultured from dead rabbits, moribund euthanized rabbits, and euthanized surviving rabbits to look for the presence or absence of *B. anthracis*. Bacteremia data are summarized in Table 3. Overall, 94% of the rabbits (17 of 18) that were found dead or were moribund euthanized had a positive *B. anthracis* blood culture while 83% (15 of 18) found dead or moribund euthanized had a positive *B. anthracis* spleen culture. All rabbits that survived until euthanized at the end of the study (Study Day 34) had negative blood and spleen cultures for *B. anthracis*.

In conclusion, after exposure to anthrax spores, the intramuscular (IM) administration of the claimed high-affinity anti-Protective Antigen (anti-PA) monoclonal antibody provides complete protection, and the bioavailability of the claimed antibody by the IM route is similar to that of the intravascular (IV) route. Furthermore, the preceding example also demonstrates that the co-administration of an anti-anthrax antibody to Protective Antigen and an antibiotic result in greater survival than antibiotic alone.

Example 3

Primate Spore Challenge Model Post-Exposure with or without Antibiotics

The primary goals of the primate PK study were to generate pharmacokinetic profiles of the claimed anti-PA antibody when administered through intravascular (IV) and intramuscular (IM) routes and to establish a dose dependency of IM administration of the anti-PA antibody. Cynomolgus monkeys (3/group) were given a single dose of anti-PA IV (5 mg/kg) by slow push (3-5 minutes) or IM (5 mg/kg or 10 mg/kg) by half-volume injections (0.4-0.8 mL/kg) administered to each thigh. Anthim levels in sera were analyzed by anti-PA ELISA pre-injection, at 1, 2, 4, 6, 24, and 32 hours post-injection, and at 3, 4, 5, 6, 7, 9, 11, and 13 days post-injection.

The pharmacokinetics in cynomolgus monkeys were characterized by lower clearance and a small volume of distribution at a steady-state. The terminal $T_{1/2}$ of the anti-PA by both routes was 7.9 (males) to 9.7 (females) days. The bioavailability of IM anti-PA averaged 83% as compared to IV administration. FIG. 4 demonstrates the results of these studies. No significant difference in pharmacokinetics was observed based on gender, except for AUC in the 5 mg/kg IM dose group, and AUC (0-inf) was linear by dose. In conclusion, the bioavailability of the claimed anti-PA antibody by the IM route in monkeys is similar to that of the IV route and represents a previously unstudied route of administration.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A method of preventing the development of inhalation anthrax in a human subject that has been exposed to *B. anthracis* spores, the method comprising administering intramuscularly a composition comprising an antibody which neutralizes *B. anthracis* toxin to the subject and further comprising administering at least one antibiotic to the subject to thereby preventing the development of inhalation anthrax in a human subject that has been exposed to *B. anthracis* spores, wherein the antibody the light chain variable region set forth as amino acid residues 1-107 in SEQ ID NO:2 and the heavy chain variable region amino acid sequence set forth as amino acid residues 1-119 in SEQ ID NO:1.

2. A method of preventing the development of inhalation anthrax in a human subject prior to exposure to *B. anthracis* spores, the method comprising administering intramuscularly a composition comprising an antibody which neutralizes *B. anthracis* toxin to the subject and further comprising administering at least one antibiotic to the subject to thereby preventing the development of inhalation anthrax in a human subject that prior to exposure to *B. anthracis* spores, wherein the antibody or binding molecule comprises the light chain variable region set forth as amino acid residues 1-107 in SEQ ID NO:2 and the heavy chain variable region amino acid sequence set forth as amino acid residues 1-119 in SEQ ID NO:1.

3. A method of treating inhalation anthrax in a human subject that has been exposed to *B. anthracis* spores, the method comprising administering intramuscularly a composition comprising an antibody which neutralizes *B. anthracis* toxin to the subject and further comprising administering at least one antibiotic to the subject to thereby treat inhalation anthrax in a human subject that has been exposed to *B. anthracis* spores, wherein the antibody comprises the light chain variable region set forth as amino acid residues 1-107 in SEQ ID NO:2 and the heavy chain variable region amino acid sequence set forth as amino acid residues 1-119 in SEQ ID NO:1.

4. The method of any one of claims 1-3, wherein the antibody has a $K_d$ of 2 nM to 15 nM.

5. The method of any one of claims 1-3, wherein the antibody comprises a human Fc region.

6. The method of claim 5, wherein the human Fc region is of the IgG1 isotype.

7. The method of any one of claims 1-3, wherein the antibody is given at a dose of 20-50 mg intramuscularly.

8. The method of any one of claims 1-3, wherein the antibody is given at a dose of 30-50 mg intramuscularly.

9. The method of any one of claims 1-3, wherein the antibody is given at a dose of at least about 38 mg intramuscularly.

10. The method of claim 1 or claim 3, wherein the antibody is administered 3 hours after exposure to exposure to *B. anthracis* spores.

11. The method of claim 1 or claim 3, wherein the antibody is administered 6 hours after exposure to exposure to *B. anthracis* spores.

12. The method of claim 1 or claim 3, wherein the antibody is administered 9 hours after exposure to exposure to *B. anthracis* spores.

13. The method of claim 1 or claim 3, wherein the antibody is administered 12 hours after exposure to exposure to *B. anthracis* spores.

14. The method of claim 1 or claim 3, wherein the antibody is administered 15 hours after exposure to exposure to *B. anthracis* spores.

15. The method of claim 1 or claim 3, wherein the antibody is administered 18 hours after exposure to exposure to *B. anthracis* spores.

16. The method of claim 1 or claim 3, wherein the antibody is administered 24 hours after exposure to exposure to *B. anthracis* spores.

17. The method of claim 1 or claim 3, wherein the antibody is administered 36 hours after exposure to exposure to *B. anthracis* spores.

18. The method of any one of claims 1-3, wherein the antibiotic is a fluoroquinolone antibiotic.

19. The method of claim 18, wherein the fluoroquinolone antibiotic is levofloxacin.

20. The method of claim 18, wherein the fluoroquinolone antibiotic is ciprofloxacin.

21. The method of any one of claims 1-3, wherein the antibody is selected from the group consisting of: a Fab fragment, an Fab' fragment, an F(ab')2 fragment, an Fv fragment, an scAb molecule, and an scFv molecule.

* * * * *